US008277379B2

(12) United States Patent
Lau et al.

(10) Patent No.: US 8,277,379 B2
(45) Date of Patent: Oct. 2, 2012

(54) METHODS AND APPARATUS FOR THE TREATMENT OF MENOMETRORRHAGIA, ENDOMETRIAL PATHOLOGY, AND CERVICAL NEOPLASIA USING HIGH INTENSITY FOCUSED ULTRASOUND ENERGY

(75) Inventors: Michael P. H. Lau, Edmonds, WA (US);
Nelson Teng, Palo Alto, CA (US);
Shahram Vaezy, Seattle, WA (US);
Alexander Lebedev, Seattle, WA (US);
Michael William Lau, Edmonds, WA (US); Michael J. Connolly, Seattle, WA (US)

(73) Assignee: Mirabilis Medica Inc., Bothell, WA (US)

( * ) Notice: Subject to any disclaimer, the term of this patent is extended or adjusted under 35 U.S.C. 154(b) by 1572 days.

(21) Appl. No.: 11/735,279

(22) Filed: Apr. 13, 2007

(65) Prior Publication Data

US 2007/0232913 A1 Oct. 4, 2007

Related U.S. Application Data

(63) Continuation-in-part of application No. 11/623,705, filed on Jan. 16, 2007, now abandoned.

(60) Provisional application No. 60/791,654, filed on Apr. 13, 2006, provisional application No. 60/758,797, filed on Jan. 13, 2006.

(51) Int. Cl.
*A61B 8/00* (2006.01)
(52) U.S. Cl. .............................. 600/439; 601/2; 600/459
(58) Field of Classification Search .......... 600/437–463; 601/1–4
See application file for complete search history.

(56) References Cited

U.S. PATENT DOCUMENTS

| 3,470,868 A | 10/1969 | Krause |
| 3,480,002 A | 11/1969 | Flaherty |
| 3,676,584 A | 7/1972 | Plakas |

(Continued)

FOREIGN PATENT DOCUMENTS

EP 0301360 B1 2/1989

(Continued)

OTHER PUBLICATIONS

Daum, D.R., and Hynynen, K., "A 256-Element Ultrasonic Phased Array System for the Treatment of Large Volumes of Deep Seated Tissue," IEEE Transactions on Ultrasonics, Ferroelectrics, and Frequency Control 46(5):1254-1268, Sep. 1999.

(Continued)

*Primary Examiner* — Sanjay Cattungal
(74) *Attorney, Agent, or Firm* — Christensen O'Connor Johnson Kindness PLLC

(57) ABSTRACT

A probe having a high intensity focused ultrasound (HIFU) transducer is positioned in a female patient. The HIFU transducer is deployed within the vagina of the patient outside of the cervix and uterine cavity and is configured to direct HIFU energy to a treatment site within the uterus of the patient. An imaging component positioned relative to the patient images a portion of the patient's uterus that includes the treatment site to help guide the delivery of the HIFU energy to the treatment site. A liquid medium may be infused into the uterine cavity of the patient where it is maintained during imaging and delivery of the HIFU therapy. The HIFU transducer produces a thermal heating of tissue at a focus within the treatment site to initiate necrosis of the tissue. The location of the focus is controlled in accordance with an image obtained by the imaging component.

15 Claims, 13 Drawing Sheets

U.S. PATENT DOCUMENTS

| | | | |
|---|---|---|---|
| 3,941,112 | A | 3/1976 | Habert |
| 4,059,098 | A | 11/1977 | Murdock |
| 4,097,835 | A | 6/1978 | Green |
| 4,185,502 | A | 1/1980 | Frank |
| 4,282,755 | A | 8/1981 | Gardineer |
| 4,347,850 | A | 9/1982 | Kelly-Fry |
| 4,484,569 | A | 11/1984 | Driller |
| 4,742,829 | A | 5/1988 | Law |
| 4,756,313 | A | 7/1988 | Terwilliger |
| 4,835,689 | A | 5/1989 | O'Donnell |
| 4,858,613 | A | 8/1989 | Fry |
| 4,865,042 | A | 9/1989 | Umemura |
| 4,893,624 | A | 1/1990 | Lele |
| 5,005,579 | A | 4/1991 | Wurster |
| 5,036,855 | A | 8/1991 | Fry |
| 5,080,101 | A | 1/1992 | Dory |
| 5,080,102 | A | 1/1992 | Dory |
| 5,080,660 | A | 1/1992 | Buelna |
| 5,117,832 | A | 6/1992 | Sanghvi |
| 5,234,429 | A | 8/1993 | Goldhaber |
| 5,271,402 | A | 12/1993 | Yeung |
| 5,391,140 | A | 2/1995 | Schaetzle |
| 5,441,499 | A | 8/1995 | Fritzsch |
| 5,471,988 | A | 12/1995 | Fujio |
| 5,474,071 | A | 12/1995 | Chapelon |
| 5,492,126 | A | 2/1996 | Hennige |
| 5,520,188 | A | 5/1996 | Hennige |
| 5,558,092 | A | 9/1996 | Unger |
| 5,619,999 | A | 4/1997 | Von Behren |
| 5,666,954 | A | 9/1997 | Chapelon |
| 5,720,287 | A | 2/1998 | Chapelon |
| 5,762,066 | A | 6/1998 | Law |
| 5,769,790 | A | 6/1998 | Watkins |
| 5,810,007 | A | 9/1998 | Holupka |
| 5,882,302 | A | 3/1999 | Driscoll, Jr. |
| 5,976,092 | A | 11/1999 | Chinn |
| 5,993,389 | A | 11/1999 | Driscoll, Jr. |
| 6,002,251 | A | 12/1999 | Sun |
| 6,007,499 | A | 12/1999 | Martin |
| 6,042,556 | A | 3/2000 | Beach |
| 6,050,943 | A | 4/2000 | Slayton |
| 6,083,159 | A | 7/2000 | Driscoll, Jr. |
| 6,126,607 | A | 10/2000 | Whitmore, III |
| 6,196,972 | B1 | 3/2001 | Moehring |
| 6,217,530 | B1 | 4/2001 | Martin |
| 6,254,601 | B1 | 7/2001 | Burbank |
| 6,267,734 | B1 | 7/2001 | Ishibashi |
| 6,315,741 | B1 | 11/2001 | Martin |
| 6,390,973 | B1 | 5/2002 | Ouchi |
| 6,425,867 | B1 * | 7/2002 | Vaezy et al. ............... 600/439 |
| 6,432,067 | B1 | 8/2002 | Martin |
| 6,451,013 | B1 | 9/2002 | Bays |
| 6,461,314 | B1 | 10/2002 | Pant |
| 6,488,639 | B1 | 12/2002 | Ribault |
| 6,500,133 | B2 | 12/2002 | Martin |
| 6,537,224 | B2 | 3/2003 | Mauchamp |
| 6,602,251 | B2 | 8/2003 | Burbank |
| 6,613,004 | B1 | 9/2003 | Vitek |
| 6,626,855 | B1 * | 9/2003 | Weng et al. ............... 601/3 |
| 6,633,658 | B1 | 10/2003 | Dabney |
| 6,645,162 | B2 | 11/2003 | Friedman |
| 6,666,835 | B2 | 12/2003 | Martin |
| 6,676,601 | B1 | 1/2004 | Lacoste |
| 6,692,450 | B1 | 2/2004 | Coleman |
| 6,716,184 | B2 * | 4/2004 | Vaezy et al. ............... 601/3 |
| 6,719,694 | B2 | 4/2004 | Weng |
| 6,740,082 | B2 | 5/2004 | Shadduck |
| 6,764,488 | B1 | 7/2004 | Burbank |
| 6,840,936 | B2 | 1/2005 | Sliwa, Jr. |
| 6,936,046 | B2 | 8/2005 | Hissong |
| 7,063,666 | B2 | 6/2006 | Weng |
| 7,105,007 | B2 | 9/2006 | Hibler |
| 7,175,596 | B2 | 2/2007 | Vitek |
| 7,258,674 | B2 | 8/2007 | Cribbs |
| 7,297,116 | B2 * | 11/2007 | Varghese et al. ............... 600/438 |
| 7,358,226 | B2 * | 4/2008 | Dayton et al. ............... 514/1.2 |
| 7,452,357 | B2 | 11/2008 | Vlegele |
| 7,470,241 | B2 * | 12/2008 | Weng et al. ............... 601/3 |
| 7,473,224 | B2 | 1/2009 | Makin |
| 7,520,856 | B2 * | 4/2009 | Vaezy et al. ............... 600/439 |
| 7,591,794 | B2 * | 9/2009 | Lacoste et al. ............... 601/2 |
| 7,686,763 | B2 * | 3/2010 | Vaezy et al. ............... 600/439 |
| 7,699,782 | B2 | 4/2010 | Angelsen |
| 7,850,626 | B2 * | 12/2010 | Vaezy et al. ............... 601/2 |
| 7,918,795 | B2 * | 4/2011 | Grossman ............... 600/439 |
| 2001/0012934 | A1 | 8/2001 | Chandrasekaran |
| 2002/0029036 | A1 | 3/2002 | Goble |
| 2002/0065512 | A1 | 5/2002 | Fjield |
| 2002/0120259 | A1 | 8/2002 | Lettice |
| 2003/0004439 | A1 * | 1/2003 | Pant et al. ............... 601/2 |
| 2003/0028111 | A1 * | 2/2003 | Vaezy et al. ............... 600/439 |
| 2003/0060736 | A1 | 3/2003 | Martin |
| 2003/0233045 | A1 | 12/2003 | Vaezy |
| 2004/0030268 | A1 * | 2/2004 | Weng et al. ............... 601/2 |
| 2004/0030269 | A1 | 2/2004 | Horn |
| 2004/0082859 | A1 | 4/2004 | Schaer |
| 2004/0153126 | A1 | 8/2004 | Okai |
| 2004/0242999 | A1 | 12/2004 | Vitek |
| 2004/0243201 | A1 | 12/2004 | Goldman |
| 2005/0038340 | A1 * | 2/2005 | Vaezy et al. ............... 600/439 |
| 2005/0084538 | A1 * | 4/2005 | Dayton et al. ............... 424/489 |
| 2005/0085726 | A1 * | 4/2005 | Lacoste et al. ............... 600/439 |
| 2005/0101854 | A1 | 5/2005 | Larson |
| 2005/0154431 | A1 | 7/2005 | Quistgaard |
| 2005/0203399 | A1 * | 9/2005 | Vaezy et al. ............... 600/439 |
| 2005/0256405 | A1 | 11/2005 | Makin |
| 2005/0267454 | A1 | 12/2005 | Hissong |
| 2006/0052701 | A1 | 3/2006 | Carter |
| 2006/0189972 | A1 * | 8/2006 | Grossman ............... 606/32 |
| 2006/0264748 | A1 | 11/2006 | Vaezy |
| 2007/0066990 | A1 * | 3/2007 | Marsella et al. ............... 606/193 |
| 2007/0194658 | A1 | 8/2007 | Zhang |
| 2007/0197918 | A1 | 8/2007 | Vitek |
| 2007/0232913 | A1 * | 10/2007 | Lau et al. ............... 600/439 |
| 2007/0238994 | A1 | 10/2007 | Stecco |
| 2007/0239011 | A1 * | 10/2007 | Lau et al. ............... 600/439 |
| 2008/0039724 | A1 | 2/2008 | Seip |
| 2008/0051656 | A1 * | 2/2008 | Vaezy et al. ............... 600/439 |
| 2008/0071165 | A1 | 3/2008 | Makin |
| 2008/0086036 | A1 | 4/2008 | Hartley |
| 2008/0125771 | A1 | 5/2008 | Lau |
| 2008/0221647 | A1 | 9/2008 | Chamberland |
| 2008/0281314 | A1 | 11/2008 | Johnson |
| 2008/0319436 | A1 | 12/2008 | Daniel |
| 2009/0036774 | A1 * | 2/2009 | Weng et al. ............... 600/439 |
| 2009/0088636 | A1 * | 4/2009 | Lau et al. ............... 600/439 |
| 2009/0228001 | A1 | 9/2009 | Pacey |
| 2009/0326420 | A1 | 12/2009 | Moonen |
| 2011/0087100 | A1 * | 4/2011 | Grossman ............... 600/439 |
| 2011/0201929 | A1 * | 8/2011 | Vaezy et al. ............... 600/439 |

FOREIGN PATENT DOCUMENTS

| | | |
|---|---|---|
| EP | 0614651 A1 | 9/1994 |
| EP | 0734742 A2 | 10/1996 |
| EP | 1 726 267 A2 | 11/2006 |
| JP | 05023336 A | 2/1993 |
| JP | 2001-61847 A | 3/2001 |
| JP | 2002-536040 A | 10/2002 |
| JP | 2004-534582 A | 11/2004 |
| WO | 93/17646 A2 | 9/1993 |
| WO | 94/27502 A1 | 12/1994 |
| WO | 95/20360 A1 | 8/1995 |
| WO | 97/00646 A1 | 1/1997 |
| WO | 00/45706 A1 | 8/2000 |
| WO | 01/71380 A2 | 9/2001 |
| WO | 02/100486 A1 | 12/2002 |
| WO | 03/002189 A2 | 1/2003 |
| WO | 2004/073524 A1 | 9/2004 |
| WO | 2005/000097 A2 | 1/2005 |
| WO | 2006097661 A1 | 9/2006 |

OTHER PUBLICATIONS

Enholm, J.K., et al., "Improved Volumetric MR-HIFU Ablation by Robust Binary Feedback Control," IEEE Transactions on Biomedical Engineering 57(1):103-113, Jan. 2010.

Mougenot, C., et al., "Automatic Spatial and Temporal Temperature Control for MR-Guided Focused Ultrasound Using Fast 3D MR Thermometry and Multispiral Trajectory of the Focal Point," Magnetic Resonance in Medicine 52:1005-1015, 2004.

Mougenot, C., et al., "Three-Dimensional Spatial and Temporal Temperature Control with MR Thermometry-Guided Focused Ultrasound (MRgHIFU)," Magnetic Resonance in Medicine 61:603-614, 2009.

Ngo, F.C., et al., "An Experimental Analysis of a Sector-Vortex Phased Array Prototype," Ultrasonics Symposium, pp. 999-1002, 1989.

Rabkin, B.A., et al., "Hyperecho in Ultrasound Images of HIFU Therapy: Involvement of Cavitation," Ultrasound in Medicine and Biology 31(7):947-956, Jul. 2005.

Umemura, S.-I., and C.A. Cain, "Acoustical Evaluation of a Prototype Sector-Vortex Phased-Array Applicator," IEEE Transactions on Ultrasonics, Ferroelectrics, and Frequency Control, 39(1)32-38, Jan. 1992.

Extended European Search Report dated Feb. 26, 2010, issued in corresponding European Patent Application No. 07811847.8, filed Apr. 13, 2007, 7 pages.

International Search Report dated May 11, 2010, in International Application No. PCT/US2009/059589, filed Oct. 5, 2009, 5 pages.

International Search Report and Written Opinion mailed May 18, 2010, issued in corresponding International Application No. PCT/US2009/053050, filed Aug. 6, 2009, 15 pages.

Cain, C.A., and S.-I. Umemura, "Concentric-Ring and Sector-Vortex Phased-Array Applicators for Ultrasound Hyperthermia," IEEE Transactions on Microwave Theory and Techniques 34(5):542-551, May 1986.

Chapelon, J.Y., et al., "The Feasibility of Tissue Ablation Using High Intensity Electronically Focused Ultrasound," Proceedings of the IEEE Ultrasonics Symposium 1993, Baltimore, Oct. 31-Nov. 3, 1993, pp. 1211-1214.

Chen, L., et al., "Effect of Blood Perfusion on the Ablation of Liver Parenchyma With High-Intensity Focused Ultrasound," Physics in Medicine and Biology 38(11):1661-1673, Nov. 1993.

Cheng, S.-Q., et al., "High-Intensity Focused Ultrasound in the Treatment of Experimental Liver Tumour," Journal of Cancer Research and Clinical Oncology 123(4):219-223, Apr. 1997.

Coad, J.E., "Thermal Fixation: A Central Outcome of Hyperthermic Therapies," Proceedings of the SPIE Conference on Thermal Treatment of Tissue: Energy Delivery and Assessment III 5698:15-22, San Jose, Calif., Jan. 23, 2005.

Delon-Martin, C., et al., "Venous Thrombosis Generation by Means of High-Intensity Focused Ultrasound," Ultrasound in Medicine & Biology 21(1):113-119, 1995.

Friedland, F., "Ultrasonic Therapy," American Journal of Nursing 59(9):1272-1275, Sep. 1959.

Fry, F.J., "Recent Bioeffects With Ultrasound on the Reproductive System and Solid Tumors," Journal of the Acoustical Society of America 63(Suppl. 1):S13, May 1978.

Hallberg, L., et al., "Menstrual Blood Loss—A Population Study: Variation at Different Ages and Attempts to Define Normality," Acta Obstetricia et Gynecologica Scandinavica 45(3):320-351, 1966.

Lee, J.M., et al., "Comparison of Wet Radiofrequency Ablation With Dry Radiofrequency Ablation and Radiofrequency Ablation Using Hypertonic Saline Preinjection: Ex Vivo Bovine Liver," Korean Journal of Radiology 5(4):258-265, Dec. 2004.

Lee, J.M., et al., "Wet Radio-Frequency Ablation Using Multiple Electrodes: Comparative Study of Bipolar Versus Monopolar Modes in the Bovine Liver," European Journal of Radiology 54:408-417, Jun. 2005.

Orsini-Meinhard, K., "UW Tech-Transfer Program Putting Discoveries to Work," The Seattle Times, May 27, 2007, 8 pages.

Rabkin, B.A., et al., "Biological and Physical Mechanisms of HIFU-Induced Hyperecho in Ultrasound Images," Ultrasound in Medicine & Biology 32(11):1721-1729, Nov. 2006.

Sanghvi, N.T., et al., "High Intensity Focused Ultrasound (HIFU) for the Treatment of Rectal Tumors: A Feasibility Study," Proceedings of IEEE Ultrasonics Symposium 3:1895-1898, Cannes, France, Nov. 1-4, 1994.

"ThermoDox™ Animal Studies to Be Presented at 6th International Symposium on Therapeutic Ultrasound in Oxford, England," Aug. 30-Sep. 2, 2006, Celsion, Inc., <http://www.celsion.com/news/releasedetail.cfm> [retrieved Oct. 8, 2007], 2 pages.

"ThermoDox™: Heat-Activated Liposome Drug," © 2007 Celsion, Inc., <http://www.celsion.com/products/ThermoDox.cfm> [retrieved Oct. 8, 2007], 3 pages.

Vaezy, S., et al., "Image-Guided Acoustic Therapy," Annual Review of Biomedical Engineering 3:375-390, Aug. 2001.

Winter, T.C., et al., "Focal Tumor Ablation: A New Era in Cancer Therapy," Ultrasound Quarterly 22(3):204-209, Sep. 2006.

Zanelli, C.I., et al., "Design and Characterization of a 10 cm Annular Array Transducer for High Intensity Focused Ultrasound (HIFU) Applications," Proceedings of the IEEE Ultrasonics Symposium 3:1887-1890, Cannes, France, Nov. 1-4, 1994.

Mittleman, R.S., et al., "Use of the Saline Infusion Electrode Catheter for Improved Energy Delivery and Increased Lesion Size in Radiofrequency Catheter Ablation," Pacing and Clinical Electrophysiology 18(5, Pt. 1):953-1081, May 1995.

International Search Report and Written Opinion mailed Oct. 26, 2010, issued in International Application No. PCT/US2010/026565, filed Mar. 8, 2010, 10 pages.

International Search Report dated Jun. 26, 2009, in International Application No. PCT/US2008/082829, filed Nov. 7, 2008.

Notice of Reasons for Rejection mailed Mar. 12, 2012, issued in corresponding Japanese Patent Application No. 2009-505639, filed Apr. 13, 2007, 7 pages.

\* cited by examiner

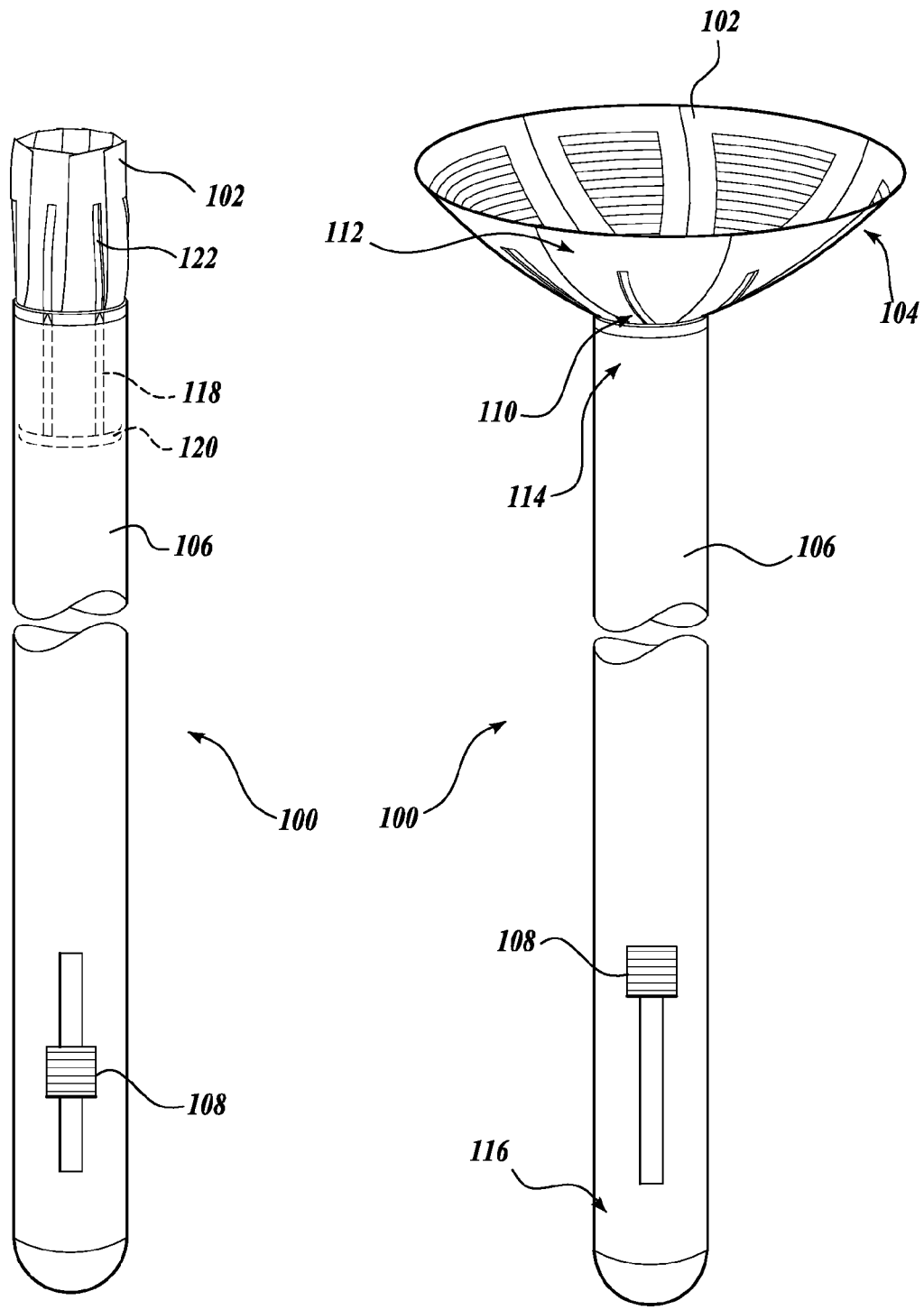

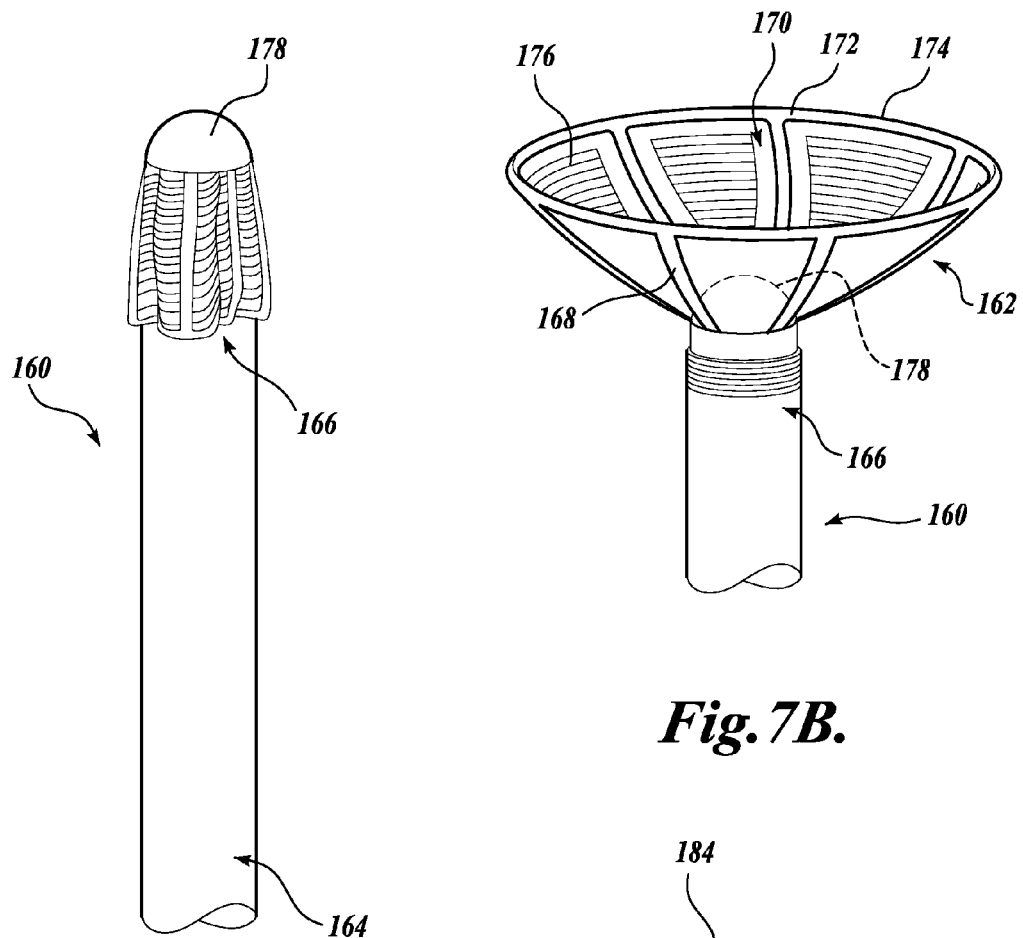
*Fig.7A.*
*Fig.7B.*
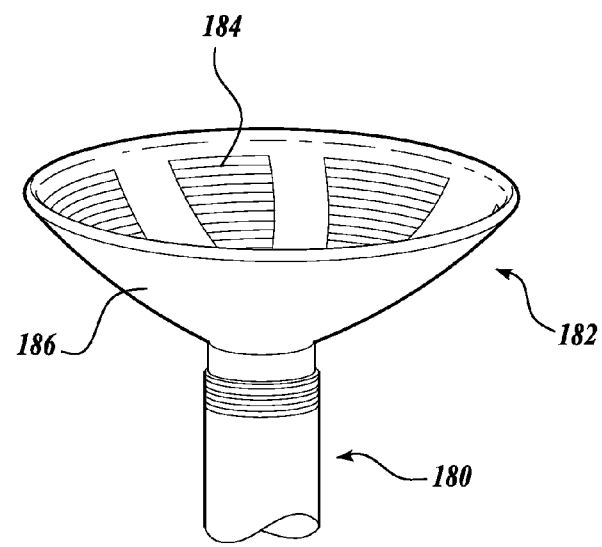
*Fig.8.*

METHODS AND APPARATUS FOR THE TREATMENT OF MENOMETRORRHAGIA, ENDOMETRIAL PATHOLOGY, AND CERVICAL NEOPLASIA USING HIGH INTENSITY FOCUSED ULTRASOUND ENERGY

CROSS-REFERENCES TO RELATED APPLICATIONS

This application claims the benefit of the filing date of U.S. Provisional Patent Application No. 60/791,654, filed Apr. 13, 2006, and further is a continuation-in-part of U.S. patent application Ser. No. 11/623,705, filed Jan. 16, 2007, which claims the benefit of U.S. Provisional Patent Application No. 60/758,797, filed Jan. 13, 2006.

FIELD OF THE INVENTION

The present application is directed to methods and apparatus that provide therapeutic treatment of internal pathological conditions using high-intensity focused ultrasound energy.

BACKGROUND

The cyclic shedding of the endometrium is the cause of menses. Prolonged, irregular, or excessive menstrual bleeding, a condition termed menometrorrhagia, has a prevalence of over 20% (Hallberg, L., et al., *Acta Obstet. Gynecol. Scand.*, 45:320-51, 1966). Hysteroscopic endometrial ablation, initially by using laser then popularized by rollerball endometrial ablation, has been in use by gynecologists for over 20 years. Different energy modalities, including hot water, hot water circulating within a balloon, cryotherapy, RF energy, and microwave, have also been used to ablate the endometrium in the treatment of menometrorrhagia. However, all these treatment modalities involve invasive means; that is, all of them require instruments to be inserted through the cervix into the uterine cavity to perform the treatment. In all cases, general, regional, or local anesthesia are required to accomplish the invasive procedure.

Additionally, cervical intraepithelial neoplasia (CIN) and HPV-related lesions on the uterine cervix have a very high prevalence among women, even at an early age. A percentage of the cervical lesions can be related to invasive cervical cancer if left untreated. CIN lesions, especially those involving the endocervical canal, need to be treated to remove all the diseased tissue. Traditionally, cold knife cone biopsy has been used to excise the cervical tissue for treatment. Laser excision and vaporization, cryotherapy, electric cautery and LEEP excision are the other treatment modalities. One concern of these treatment methods is the non-selective destruction of cervix tissue in the general area of the CIN lesions. While the CIN lesions involve only the superficial layer of tissue, the above treatment modalities destroy far more underlying normal cervical tissue than necessary for the purpose of elimination of the lesions. The consequence of excessive tissue damage can lead to cervical incompetence, cervical stenosis, cervical deformities; all can potentially affect future conception rate and pregnancy wastage rate.

More recently, high-intensity focused ultrasound (HIFU) has emerged as a precise, non-surgical, minimally-invasive treatment for benign and malignant tumors. (See, e.g., S. Vaezy, M. Andrew, P. Kaczkowski et al., "Image-guided acoustic therapy," Annu. Rev. Biomed. Eng. 3, 375-90 (2001)). At focal intensities 4-5 orders of magnitude greater than diagnostic ultrasound (typically about 0.1 W/cm$^2$), HIFU (typically about 1000-10,000 W/cm$^2$) can induce lesions or tissue necrosis at a small location deep in tissue while leaving tissue between the ultrasound source and focus unharmed. Tissue necrosis is a result of focal temperatures typically exceeding 70° C. which can occur with relatively short intervals of HIFU exposure. HIFU is currently being used clinically for the treatment of prostate cancer and benign prostatic hyperplasia, as well as malignant bone tumor and soft tissue sarcoma. Clinical trials for HIFU treatment of breast fibroadenomas and various stage 4 primary and metastatic cancer tumors of the kidney and liver are underway.

Another example of a pathological condition in the female pelvis is a uterine fibroid, which is the most common pelvic tumor in women of reproductive age. Uterine fibroids, or leiomyoma, are benign tumors that cause abnormal uterine bleeding. The incidence of fibroids has been estimated to be 20-25% in women in their reproductive years, although autopsy studies show an incidence upwards of 75%. Approximately ⅓ of these women will have a tumor that is symptomatic requiring treatment.

A major challenge for transvaginal HIFU treatment of uterine pathologies is the deployment of a HIFU therapy transducer having an aperture of adequate size. In general, devices with a larger HIFU aperture tend to optimize the focal length of the HIFU beam and the therapeutic effect of the focused ultrasound energy. However, the size and configuration of the HIFU aperture are generally limited by the size and shape of the vaginal cavity and the location of the cervix and vaginal formices.

Further development of methods and apparatus for providing HIFU therapy in obstetrics and gynecology, as well as other fields of medical endeavor, is desired. In particular, improved methods and apparatus are needed which can provide noninvasive therapeutic treatment of abnormal uterine bleeding conditions and other obstetric and gynecologic pathological conditions. Such treatment includes ablation of the endometrium in the uterus as well as CIN and HPV-related lesions on the cervix.

SUMMARY

The following description briefly summarizes certain aspects of the present disclosure. This summary is not intended to identify all features or implementations disclosed herein, nor is it intended to identify key features or otherwise be used to define the scope of the invention claimed hereafter.

Ablation of the endometrium in the uterus can decrease or stop the cyclic menstrual flow. As described herein, HIFU energy can be used to ablate the uterine endometrium, non-invasively, to treat the problem of menometrorrhagia. Embodiments of the present invention also were developed to treat cervical neoplasia, including cervical intraepithelial neoplasia and human papilloma virus (HPV)-related lesions, by the precise application of HIFU energy to treat the lesions while limiting collateral damage to adjacent normal tissue. Described herein are methods and devices using a transvaginal approach, with real time ultrasound imaging to guide the HIFU treatment. Various configurations of imaging transducers and HIFU transducers and apertures may be used to achieve an optimal treatment modality. As further described herein, a liquid medium, including gel, may be used to enhance the imaging of the uterine cavity, the endometrium, the endocervical canal and/or the ectocervical tissue to visualize the anatomy and pathology of the target lesions. The liquid medium may also be used to enhance the treatment effects of the HIFU energy. Materials, including but not limited to physical particles, microbubbles, and drugs, can be added to the liquid medium to enhance both the imaging and the HIFU effects in the treatment of uterine pathologies, such as menometrorrhagia, endometrial pathology, and cervical neoplasia.

Disclosed herein are methods that use high intensity focused ultrasound energy for ablation of tissue in a female patient. In accordance with an embodiment, a probe having a transducer is positioned in the patient. The transducer is deployed within the vagina of the patient outside of the cervix and uterine cavity and is configured to direct HIFU energy to a treatment site within the uterus of the patient. The method further comprises positioning an imaging component relative to the patient to image a portion of the patient's uterus that includes the treatment site to help guide the delivery of the HIFU energy to the treatment site. A liquid medium is infused into the uterine cavity of the patient where it is maintained during imaging and delivery of the HIFU therapy. The HIFU transducer produces a thermal heating of tissue at a focus within the treatment site to initiate necrosis of the tissue. The location of the focus is controlled in accordance with an image obtained by the imaging component.

In accordance with another embodiment, a probe having a HIFU transducer is deployed in the vagina of the patient outside of the cervix, wherein the transducer is configured to direct HIFU energy to a treatment site at or within the cervix of the patient. When the HIFU transducer is energized, thermal heating of tissue occurs at a focus within the treatment site which initiates necrosis of the tissue. The method further includes imaging a portion of the cervix to produce an image that includes the treatment site. The image is used to control the focus and thus direct the HIFU energy to the cervical tissue being ablated.

Further disclosed herein is apparatus that can be used for ablation of tissue in a female patient using high intensity focused ultrasound energy. In accordance with an embodiment, the apparatus includes a probe, imaging component, and transport line carrying a liquid medium. A distal end of the probe includes a transducer configured to emit HIFU energy toward a treatment site within the cervix and/or uterus of the patient. The transducer is deployable in the vagina of the patient outside of the cervix and uterus. The imaging component is configured to image a portion of the patient's cervix and/or uterus that includes the treatment site to help guide the delivery of HIFU energy from the transducer to the treatment site.

The transport line is adapted for insertion through the vagina to carry the liquid medium at least to the cervix. The transport line is capable of infusing the liquid medium into the endocervical canal and/or the uterine cavity of the patient, where the liquid medium is maintained during imaging and delivery of HIFU energy to the treatment site. As with the method embodiments, the HIFU transducer is configured to produce a thermal heating of the tissue at a focus of the HIFU energy within the treatment site to initiate necrosis of the tissue. The location of the focus is controllable in accordance with an image obtained by the imaging component, thus guiding the delivery of the HIFU therapy from the probe.

In accordance with yet another embodiment, a HIFU transducer is deployed in the vagina of a patient outside of the uterine cavity, wherein the transducer is configured to direct HIFU energy into the uterine cavity to ablate a volume of endometrial tissue of the patient. The HIFU transducer is energized to produce a thermal heating that initiates necrosis of the volume of endometrial tissue. An image of at least a portion of the uterus that includes the volume of endometrial tissue being ablated is obtained, and based on the image, the delivery of HIFU energy is controlled to ablate the endometrium of the patient.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 5A and 5B illustrate an implementation of an apparatus with a collapsible HIFU therapy transducer;

FIGS. 7A and 7B illustrate an implementation of an apparatus having a HIFU therapy transducer with an inflatable support;

FIG. 8 illustrates another implementation having a HIFU therapy transducer with an inflatable support;

DETAILED DESCRIPTION

The methods and apparatus described herein are designed to deliver high-intensity focused ultrasound (HIFU) energy to a treatment site internal to a patient's body. In particular, various implementations are useful for treating female pathologies, such as pathologies of the uterus. Ablation of uterine tissue, including the endometrium and/or CIN or HPV-related lesions using HIFU energy is based on the deposit of thermal and mechanical energy, including cavitation effect, to destroy the cells in the target tissue. The extent of the target tissue to be treated is typically determined by a clinician, taking into account factors such as the nature and contour of the lesion, the volume of endometrium, and the response of the tissue to HIFU ablation. The effort and time required for HIFU treatment of the target tissue generally correlates to the volume of tissue intended to be treated.

Various implementations of apparatus described herein are also designed to facilitate the insertion of a probe with a HIFU therapy transducer through a narrow opening to various cavities of the human body. These implementations can be applied to body orifices and cavities including, but not limited to, the urinary tract, gastrointestinal tract, cardiovascular system, respiratory system, and reproductive system, as well as through endoscopes or laparoscopes for minimally-invasive surgery in various parts of the body. For purposes of illustration herein, various implementations are shown and discussed in the context of providing HIFU therapy in the female reproductive system.

Preferably, embodiments of the invention are non-invasive in use. In at least one embodiment, a transvaginal imaging and HIFU probe is positioned within the vagina outside of the cervix and uterine cavity during treatment. The non-invasive nature of this embodiment makes it generally possible to perform a procedure, such as endometrial ablation, in an office setting without general or regional anesthesia. In addition, the HIFU modality described herein has an additional advantage of real time ultrasound visualization of the target tissue and precision therapeutic effect to offer higher efficacy and safety. More precise ablation of the target tissue with limited collateral tissue damage can be attained.

Figure 1:
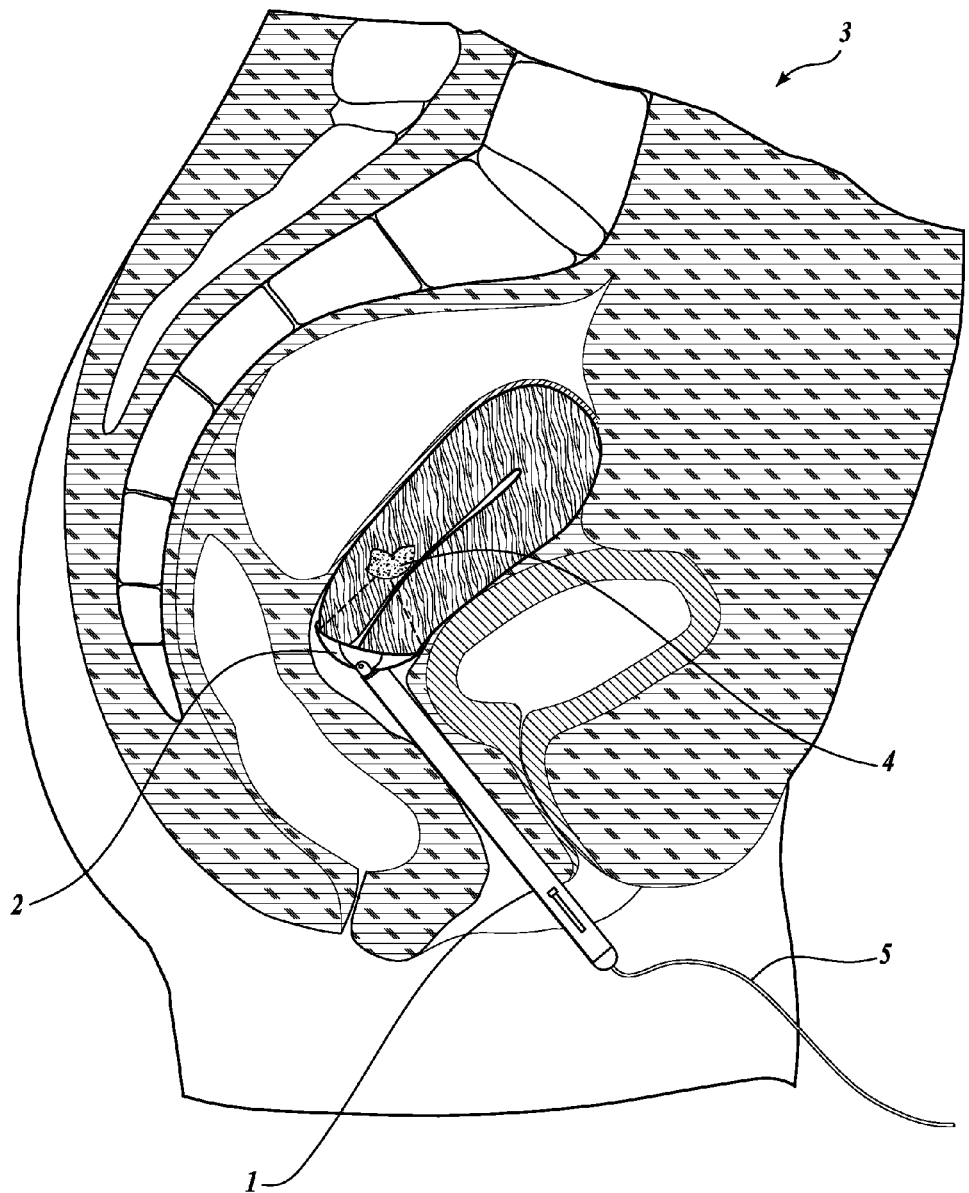
FIG. 1 illustrates in section view a possible environment in which an apparatus described herein may be used for treatment of pathologies of the female reproductive system.

FIG. 1 illustrates a probe 1 with a HIFU therapy transducer 2 that has been introduced into the vaginal cavity of a female patient 3. In this particular implementation, the HIFU therapy transducer is designed for coupling to the uterine cervix for delivering a highly focused beam of HIFU energy, depicted by dotted line, to a treatment site within the uterus. In this illustration, the treatment site is a uterine fibroid 4. As described later herein with respect to FIGS. 11 and 12, treatments site may include endometrial tissue in the uterine cavity and/or CIN or HPV-related lesions on the cervix. The HIFU therapy transducer 2 is able to direct ultrasound emissions through a constant uterine tissue medium, thereby enhancing the therapeutic, and possibly diagnostic, effects of the ultrasound energy.

An additional coupling device can be used between the transducer 2 and the cervix to optimize the ultrasound transmission. The coupling may also include a cooling component. Known in the art are various pillows filled with fluid that can provide a cooled coupling between a HIFU transducer and a mass of tissue. The probe 1, shown in FIG. 1, further includes a coupling 5 to an external source that may deliver a circulation of cooling fluid, as well as energy to the probe 1 for operating the components of the probe. The cooling fluid is used to lower the temperature of the HIFU transducer as well as the tissue surrounding the transducer, including but not limited to the cervix, to decrease the risk of collateral thermal damage from the focused HIFU beam. The coupling of the transducer 2 to the cervix further enables the clinician to manipulate the position of the cervix and uterus to optimize the HIFU treatment.

HIFU therapy transducers discussed herein have a compact state that facilitates insertion into the vaginal cavity, after which the HIFU therapy transducer is deployed to a larger state in which the transducer delivers HIFU therapy to target tissue in the body.

If desired, the probe 1 may further include an imaging component that is operable to visualize the various pelvic organs and pathologies. The imaging component may be designed to produce two-dimensional or three-dimensional visual images of the tissue of interest and/or blood flow of the tissue, as well as provide a temperature quantification of the tissue in view. Further, while the imaging system may be designed to use ultrasound energy, imaging technologies are not limited to such an energy modality.

As depicted, the therapeutic component of the HIFU transducer may be constructed with various configurations to achieve optimal focal length and aperture sizes and shapes to achieve an optimal energy delivery for therapeutic purposes. Implementations of the invention can be constructed, as described herein, to provide optimal energy delivery to intended targets, such as fibroid tumors in the uterus, as well as endometrial and cervical tissue, while also limiting collateral damage to adjacent tissue. By managing the harmonics of transducer excitation, as well as the phase and direction of energy emission, the shape and location of the focal point of the HIFU transmission can be adjusted. The selection of an appropriate HIFU transducer for implementation in the present invention is well within the knowledge of a person having ordinary skill in HIFU technology.

Elements for generating HIFU energy are well known in the art. A HIFU transducer may be configured with HIFU-generating element arranged in an annular array, for example, which may allow focal range control. Alternatively, the HIFU generating elements may be arranged in a linear array, which may allow both focal range and steering control. In yet other implementations, the elements could be arranged in a two-dimensional array, which may allow focal range and steering control in three dimensions. The latter arrangement is preferably used in concert with a two-dimensional imaging array that allows for three-dimensional ultrasound visualization. Where multiple elements are used, the elements may be phased with varying phase to allow proper focusing of the HIFU transducer on various targets in the body. Alternatively, HIFU emission from the multiple elements may be coordinated to produce a beam as if coming from a single element. Examples of HIFU transducers that may be adapted to provide HIFU therapy as disclosed herein are described, for instance, by Shahram Vaezy et al. in U.S. Patent Application Publication No. 2005/0203399, titled "Image Guided High Intensity Focused Ultrasound Device for Therapy in Obstetrics and Gynecology," the disclosure of which is incorporated herein by reference.

Figure 2:
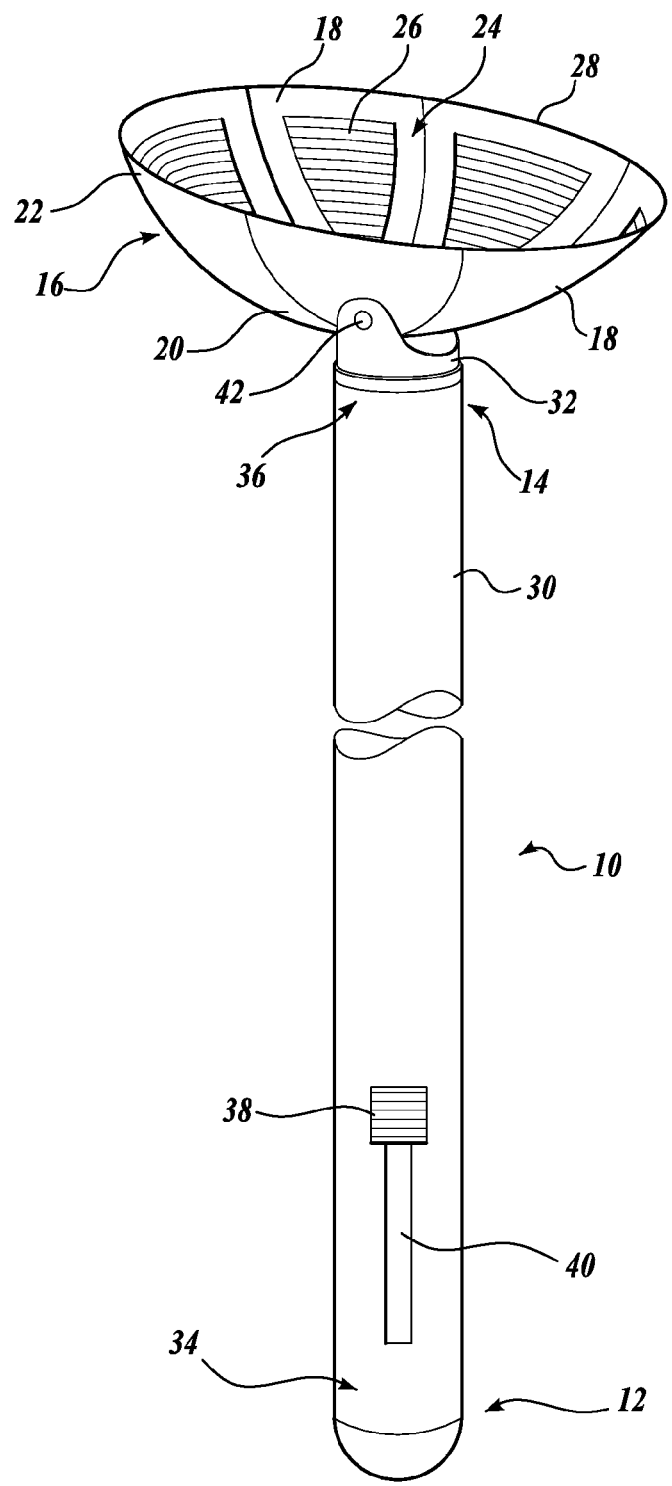
FIG. 2 illustrates the implementation of the apparatus depicted in FIG. 1.

An apparatus for delivering HIFU therapy as shown in FIG. 1 is shown in greater detail in FIG. 2. The apparatus includes an elongate probe 10 having a proximal end 12 and a distal end 14. The proximal end 12 of the probe 10 preferably has a section adapted for positioning the distal end 14 at a desired location within a body cavity when the probe 10 is inserted through an orifice into the patient's body. In this implementation, the distal end 14 of the probe 10 has a HIFU therapy transducer 16 coupled thereto. The HIFU therapy transducer 16 comprises a plurality of leaves 18. Each leaf 18, as shown, has a proximal end 20 and a distal end 22, as well as a deployment mechanism that will be discussed in greater detail below. The proximal end 20 of each leaf 18 is coupled to the distal end 14 of the probe 10.

Each leaf 18 has a front surface 24 adapted to direct HIFU energy to a treatment site in the patient's body when the HIFU therapy transducer 16 is deployed. In the implementation shown in FIG. 2, the front surface 24 of at least one of the leaves includes an active element 26 disposed thereon. The active element 26 is operable to generate HIFU energy that is directed by the transducer 16 to the treatment site, such as the fibroid shown in FIG. 1. HIFU-generating elements, as well as the signals and systems required for operating the active elements to generate HIFU energy, are well known in the art and need not be discussed in detail herein. For example, HIFU elements using piezoelectric technologies are known in the art and may be used in the implementations discussed herein.

Depending on the materials used to construct the leaves 18 and the dimension of the leaves 18 in the HIFU therapy transducer 16, the leaves 18 may each be independently coupled to the probe 10, separate from one another. For stability of the transducer 16, the leaves 18 may also be interconnected to each other if desired. In FIG. 2, the leaves 18 are constructed to collapse to a smaller state by sliding over the top of one another, thus reducing the dimension of the HIFU therapy transducer from a deployed state, as shown in FIG. 2, to a more compact state that facilitates insertion of the probe 10 into a body cavity.

Each of the leaves 18 has a deployment mechanism that is used to deploy the HIFU therapy transducer 16 to a state as shown in FIG. 2 after the probe 10 is inserted into the patient. When activated, the deployment mechanism is configured to deploy the leaves 18 by directing the distal end 22 of the leaves 18 in a radially outward direction. The leaves, thus deployed, collectively provide a bowl-shaped HIFU therapy transducer 16 having an outer edge 28 with a diameter that is larger than the diameter of the probe 10. The HIFU therapy transducer 16, when deployed, has an aperture of a size sufficient to direct a highly focused beam of HIFU energy to a treatment site in a patient. When the deployment mechanism is not activated, the collapsed leaves 18 occupy a space having a diameter smaller than the diameter of the outer edge 28 of the transducer 16 when the leaves 18 are deployed.

In the implementation shown in FIG. 2, as well as certain other implementations disclosed herein, the probe 10 includes a sleeve 30 disposed around a shaft 32. The sleeve 30 has a proximal end 34, a distal end 36, and a longitudinal axis extending therebetween. The shaft 32 is configured to slide within the sleeve 30 from a retracted position to an extended position along the longitudinal axis of the probe 10.

To assist the sliding of the shaft from the retracted to the extended position, an actuator, such as a button 38, may be provided. In FIG. 2, the button 38 is connected to the shaft 32 and slides within a groove 40 in the sleeve 30. A clinician operating the probe may grasp the button 38 and slide it within the groove 40 to the position shown in FIG. 2 to place the shaft in the extended position.

When the button 38 is slid through the groove 40 toward the proximal end 34 of the probe, the shaft 32 is pulled within the sleeve 30. As the shaft 32 is sliding inward, the leaves 18 contact the distal end 36 of the sleeve 30 and inwardly contract to be pulled within the sleeve 30. In the implementation shown, a portion of each leaf 18 is designed to slide over in front of an adjacent leaf 18 as the shaft 32 is pulled within the sleeve 30 and the leaves 18 contract.

FIG. 2 additionally illustrates a hinge 42 at the distal end 14 of the probe 10. In this implementation, the HIFU therapy transducer 16 is coupled to the distal end 14 of the probe 10 via the hinge 42. The hinge 42 has an axis about which the transducer 16 can rotate to aim the HIFU energy toward the treatment site in the patient's body, e.g., as depicted in FIG. 1.

Figures 3A, 3B, 3C:
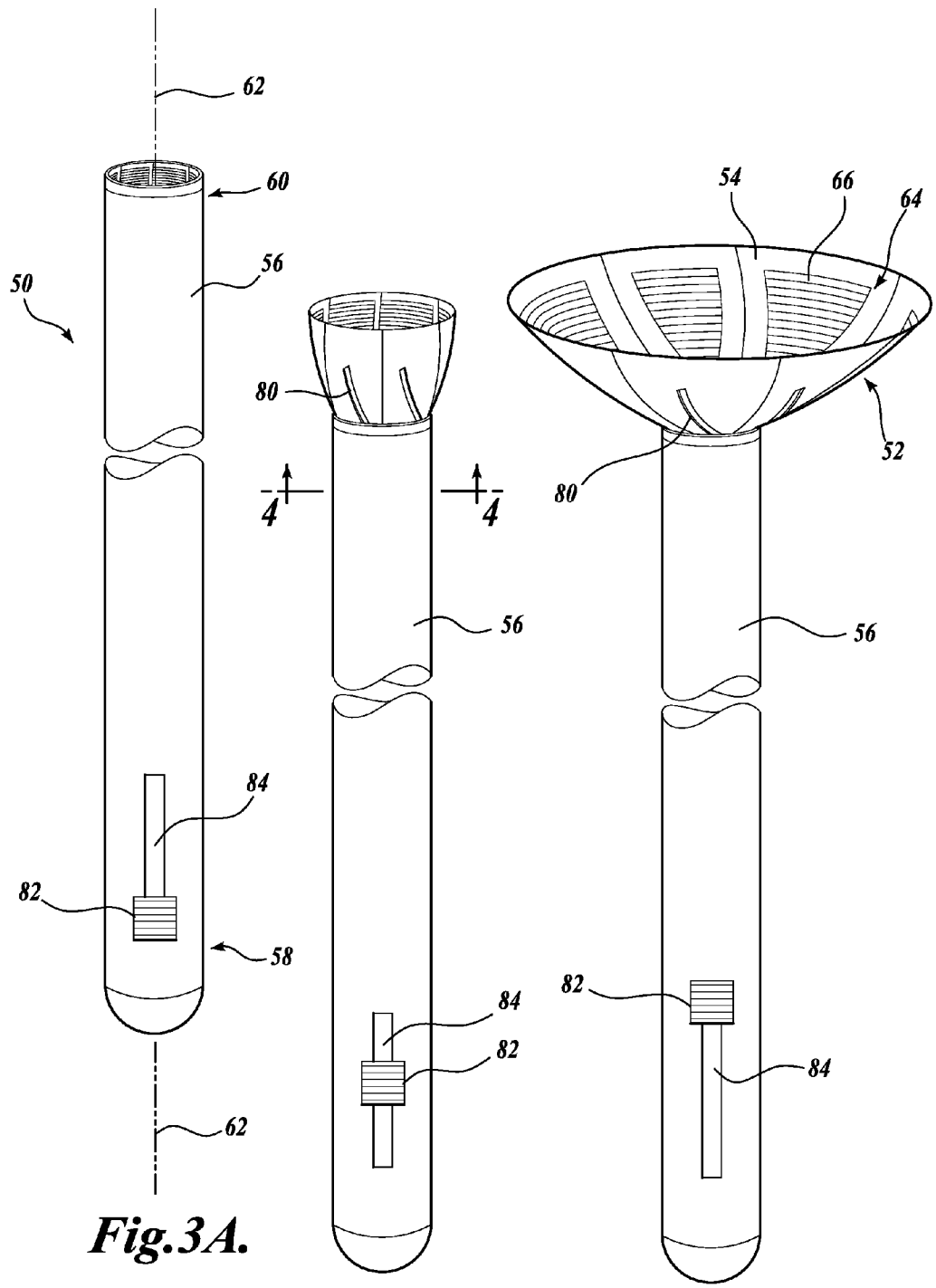
FIGS. 3A-3C illustrate an implementation of an apparatus having a retractable HIFU therapy transducer.

FIGS. 3A-3C illustrate an implementation of an elongate probe 50 having a HIFU therapy transducer 52 comprised of retractable leaves 54, similar to the probe 10 shown in FIGS. 1 and 2. The probe 50 includes a sleeve 56 disposed around a shaft 70 (FIG. 4) inside the sleeve. The sleeve 56 has a proximal end 58, a distal end 60, and a longitudinal axis 62 extending therebetween. The shaft is configured to slide inside the sleeve 56 from a retracted position, as shown in FIG. 3A, to an extended position, as shown in FIG. 3C, along the longitudinal axis 62. FIG. 3B illustrates the shaft at an intermediate stage between the retracted and extended positions.

As with the implementation shown in FIGS. 1 and 2, each leaf 54 has a front surface 64 adapted to direct HIFU energy to a treatment site when the probe 50 is inserted into a patient's body. An active element 66 disposed on the front surface 64 is operable to generate the HIFU energy that is directed to the treatment site. Although the implementation in FIGS. 3A-3C depicts multiple leaves 54 having a front surface 64 with an active element 66, not all of the leaves 54 are required to have an active element. Indeed, in at least some implementations, the front surface 64 may be designed without any active elements for generating HIFU energy. Instead, the front surface 64 of at least one of the leaves 54 is configured to reflect HIFU energy toward the treatment site, wherein the HIFU energy is received from a source that is remote from the leaf. For example, a HIFU energy source may be coupled to the probe at a location central to the HIFU therapy transducer 52 but away from the leaves 54. Alternatively, a HIFU energy source may be located separate from the probe 50. In either case, the front surface 64 of at least one of the leaves 54 is provided with a mirror-like material that reflects HIFU energy incident upon the surface 64. Materials with properties known for reflecting incident energy are readily available and recognized by persons having ordinary skill. The geometry of the leaves 54, when in a deployed state, is configured to direct the HIFU energy to a focal point at the intended treatment site in the patient.

Figure 4:
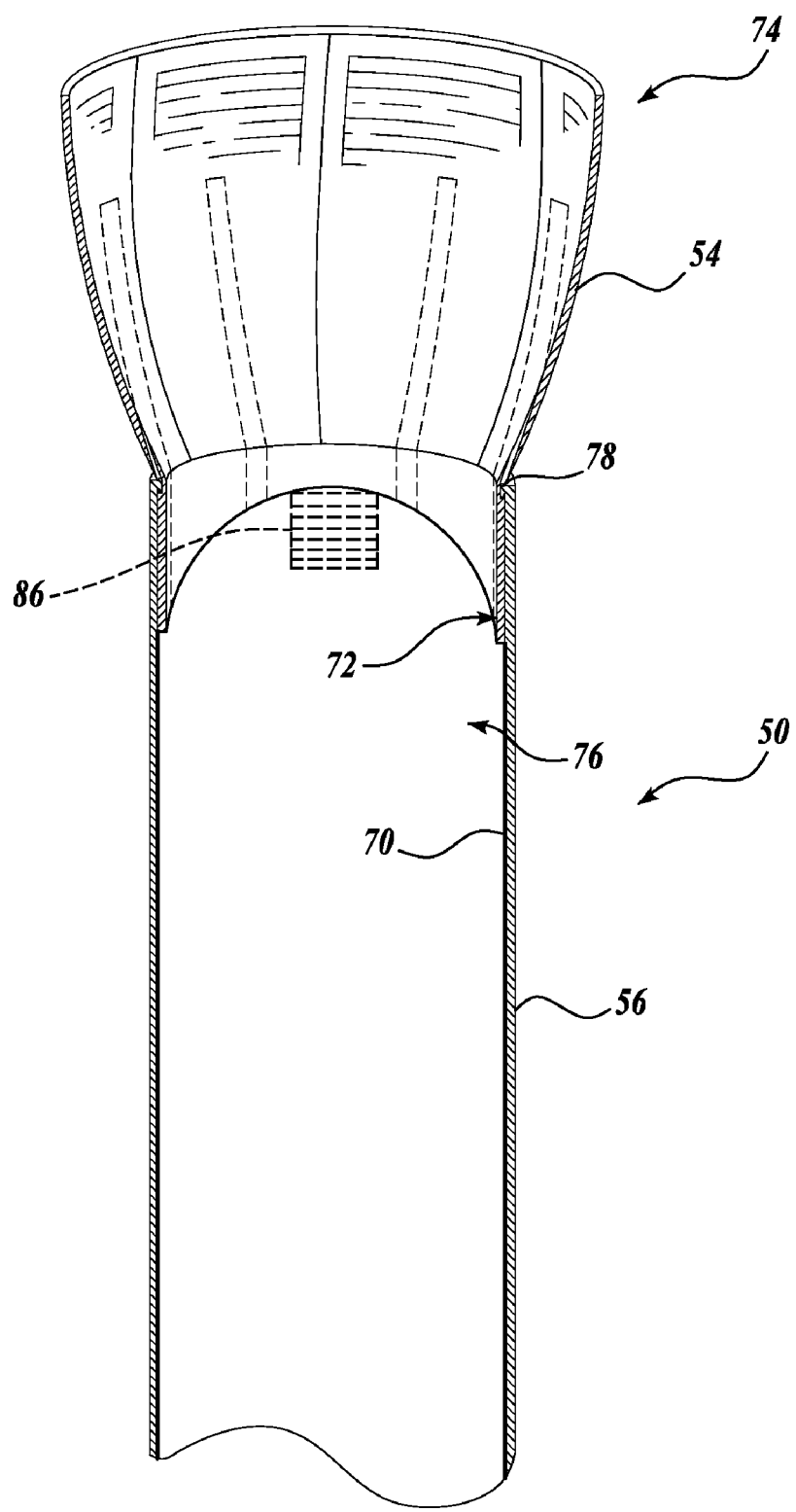
FIG. 4 illustrates a side section view of the implementation shown in FIGS. 3A-3C.

FIG. 4 illustrates a side section view of the probe 50 shown in FIG. 3B. In FIG. 4, the sleeve 56 is shown disposed around the shaft 70. Each of the leaves 54 has a proximal end 72 and a distal end 74. The proximal end 72 of each leaf 54 is coupled to a distal end 76 of the shaft 70, e.g., through a pin, adhesive, welding, or the like. Where the leaf 54 includes an active HIFU-generating element, the coupling further includes a means for conveying energy from the probe 50 to the active element, such as a wire.

Each leaf 54 further includes a deployment mechanism that, when activated, deploys the leaves 54 by directing the distal end 72 of the leaves in a radially outward direction. In the implementation shown in FIGS. 3A-3C and in FIG. 4, the deployment mechanism of each leaf includes a pin 78 that is coupled to the distal end 60 of the sleeve 56. The pin 78 is configured to slide within a groove 80 (FIGS. 3B and 3C) defined in the leaves 54.

Activation of the deployment mechanism in this implementation comprises sliding the shaft 70 within the sleeve 56 toward the extended position shown in FIG. 3C. As the shaft 70 slides upward through the sleeve 56, each leaf 54 is pushed outward from the distal end 60 of the sleeve 56. As each leaf is pushed outward, the pin 78 for each respective leaf 54 slides within the groove 80 to direct the distal end 74 of the leaf radially outward to a desired position in which the leaves collectively provide a bowl-shaped HIFU transducer 52, as shown in FIG. 3C.

In the illustrated implementation, the grooves 80 are defined at an angle relative to the longitudinal axis 62 such that the leaves 54 are directed sideways, as well as outward, when the shaft 70 is slid to the extended position. Similarly, when the shaft 70 is drawn to the retracted position shown in FIG. 3A, the pin 78 for each leaf 54 slides within the groove 80 to guide the leaf laterally and radially inward as the leaves are pulled into the sleeve 56. As depicted in FIG. 3B, at least a portion of a leaf 54 in the plurality of leaves is configured to overlap at least a portion of another leaf 54 when the leaves are retracted and held within the sleeve 56. To assist with retracting or extending the shaft 70, an actuator, such as a button 82, may be attached to the shaft 70, as shown in FIGS. 3A-3C. As with the implementation shown in FIGS. 1 and 2, the button 82 may slide within a groove 84 defined in the sleeve 56. A force exerted on the button 82 in a direction toward or away from the distal end 60 of the sleeve 56 is translated to the shaft 70 for moving the shaft 70 within the sleeve.

If desired, the pin 78 may include a detent that is configured to secure the pin within the groove 80 in each respective leaf. Furthermore, if desired, the probe 50 may be configured such that the distal end 76 of the shaft 70 extends beyond the distal end 60 of the sleeve 56 when the shaft is in the extended position, thus exposing the distal end 76 of the shaft 70 outside the sleeve 56. This latter feature may be advantageous when the probe 50 is configured with an imaging component 86 at the distal end 76 of the shaft 70. Coupling an imaging component 86 to the distal end of the shaft, or otherwise to the distal end of the probe, may assist in the process of delivering HIFU therapy to the patient.

The imaging component 86 is preferably adapted to produce an image of a portion of the patient's body that includes the treatment site receiving the HIFU energy. Conventional imaging technologies may be used. The image may help guide the delivery of HIFU energy to the treatment site. In one aspect, the imaging component may be configured to use reflected ultrasound energy to produce the image of the portion of the patient's body. Diagnostic ultrasound uses ultrasound energy at a much lower power density so as not to damage tissue.

Alternatively, the imaging component 86 may be configured to use reflected light to produce a visual image of a portion of the patient's body. Light-based imaging technologies may include elements such as fiber optic transmission and reception of light, lenses (as needed), and/or electronic charge-coupled devices (CCDs) that can receive and measure reflected light to produce an image. Reflected ultrasound energy is preferred because tissue forms and densities at various depths in the patient's body can be observed.

Where reflected ultrasound energy is used to produce an image, the emission and reception of diagnostic ultrasound energy should be synchronized with the transmission of HIFU energy so as not to obscure the image obtained by the imaging component 86. Technologies for synchronizing imaging and HIFU pulses are available in the art. See, e.g., U.S. Patent Application Publication No. 2006/0264748, titled "Interference-Free Ultrasound Imaging During HIFU Therapy, Using Software Tools," by Shahram Vaezy et al., the disclosure of which is incorporated by reference herein.

Additionally, imaging technologies may be used to provide real-time two-dimensional or three-dimensional viewing of the target site, as well as blood flow color imaging (Doppler) and temperature change quantifications of the target tissue, using ultrasound back scatter information obtained from either the HIFU transducer or the imaging component.

FIGS. 5A and 5B illustrate an implementation of a probe 100 with features similar to those shown and described with respect to FIGS. 1-4, including a plurality of leaves 102 that can be deployed to collectively provide a bowl-shaped HIFU transducer 104. As with the previously described implementations, the probe 100 further includes a sleeve 106 disposed around a shaft within the sleeve. An actuator, such as the button 108, is connected to the shaft to assist in sliding the shaft from a retracted position, as shown in FIG. 5A, to an extended position, as shown in FIG. 5B.

In contrast to the previously described implementation, the leaves 102 are coupled to the sleeve 106. More specifically, each leaf 102 has a proximal end 110 and a distal end 112. The proximal end 110 of each leaf is coupled to the distal end 114 of the sleeve 106. Furthermore, the proximal end 116 of the sleeve 104 may have a section adapted for positioning the distal end 114 at a desired location within a patient's body when the probe 100 is inserted into the patient.

As further depicted in dotted line in FIG. 5A, a plurality of spines 118 may be coupled to the distal end 120 of the shaft within the sleeve 106. When the shaft is in the retracted position, as shown in FIG. 5A, the spines 118 are held within the sleeve 106. The leaves 102 are constructed such that they can overlap one another in a collapsed configuration as shown, where the leaves 102 are capable of being grouped together to occupy a smaller space. For example, as shown in FIG. 5A, the group of leaves 102 may occupy a space having a diameter that is equal to or smaller than the diameter of the sleeve 106. Having the leaves in a collapsed state facilitates insertion of the probe 100 into a patient's body. After the probe 100 is inserted into the intended cavity of a patient's body, the leaves 102 may be deployed using a deployment mechanism, namely, the spines 118, to direct the distal end 112 of each leaf in a radially outward direction to a desired position to provide the bowl-shaped HIFU transducer 104.

Thus, in operation, activation of the deployment mechanism for FIGS. 5A and 5B comprises sliding the shaft within the sleeve 106 toward the extended position, as depicted in FIG. 5B. As the shaft is slid within the sleeve, the spines 118 emerge from the sleeve 106 and slide within grooves 122 defined in each of the leaves 102. As the spines 118 progressively enter the grooves 122, the spines 118 direct the distal end 112 of each of the leaves 102 in a radially outward direction. The spines 118 also provide support to the leaves 102 when the plurality of leaves are deployed. Pulling the shaft into the sleeve 106 toward the retracted position withdraws the spines 118 from the grooves 122, which allows the leaves 102 to collapse to the state shown in FIG. 5A.

The spines 118 may be constructed of a suitable material capable of providing support to the leaves 102 when the shaft is extended and the leaves are deployed. The spines 118 may be configured to exert an outwardly directed bias force on the leaves 102 when the shaft is extended and the spines 118 fill the grooves 122. The spines 118 are constructed to hold the leaves 104 in the deployed state, as shown in FIG. 5B. If desired, one or more stops may be defined in the distal end 114 of the sleeve 106 to engage the leaves 102 once the leaves have reached the deployed position. The outwardly-directed bias force of the spines 118 may derive from a natural characteristic of the materials used to construct the spines, such as a spine formed of a material having an outwardly-directed curve in a resting state outside the sleeve 106, which is flexible to bend to a straight non-resting state inside the sleeve 106. Alternatively, a mechanism, such as a spring, may be configured with the spines 118 to bear against the spines 118 and direct the leaves in a radially outward direction when deployed.

In another alternative implementation, a deployment mechanism comprised of springs having a first end coupled to the shaft and a second end disposed within the leaf, may be used. An implementation using springs for deployment may be visualized using the drawings in FIGS. 3A-3C, wherein the grooves 80 are filled with the second end of a spring, as described, instead of being guided by pins 78 in the sleeve 56. In this case, the second end of the springs need not be disposed at an angle as the grooves 80 are depicted. As the shaft within the sleeve 56 is slid upward to an extended position, as shown in FIG. 3C, the second end of the springs emerges from the sleeve 56 and exerts an outward bias to direct the distal end of the leaves 54 in a radially outward direction. Similarly, retracting the shaft within the sleeve 56 pulls the leaves 54 with the springs into the sleeve 56, wherein the leaves and springs are held, as shown in FIG. 3A.

In yet another implementation, a portion of the leaves, such as the leaves 102 shown in FIG. 5B, may be formed of an energy-activated shape memory alloy. The deployment mechanism of the leaves 102 in this implementation includes a coupling that connects the shape memory alloy to an energy source. Activation of the deployment mechanism comprises delivering energy from the energy source to the shape memory alloy in each leaf that causes the shape memory alloy to take a predefined shape in which the distal end of the leaves 102 are directed radially outward to provide a bowl-shaped HIFU transducer 104.

A typical shape memory alloy is made of nickel and titanium and is known for its flexibility as well as shape changing properties. The alloy dynamically changes its internal structure at certain temperatures. Structures formed with a shape memory alloy, such as the leaves 102, can be deformed at room temperature, and when the shape member alloy is heated, the alloy causes the structure to shift to a predefined shape. For example, shape memory alloys may contract when heated and then be easily stretched out again as they return to their original temperature. Energy-driven heating and cooling of a shape memory alloy can be accomplished quite quickly.

In the context of the present invention, a probe, such as the probe 100 shown in FIG. 5B (without spines 118 shown in FIG. 5A), may include a plurality of leaves 102 having a proximal end 110 coupled to the probe. Some or all of each leaf 102 may be formed of a shape memory alloy. As energy from an energy source within the probe is delivered to the shape memory alloy of the leaves, the leaves flex in a radially outward direction to provide the HIFU therapy transducer 104, as shown. In an implementation where spines 118 are used, the spines may be formed of a shape memory alloy which, being activated by the application of energy to the alloy, cause each of the spines 118 to flex in a radially outward direction, thus placing the leaves 102 in a deployed state. In such implementations, the spines 118 may or may not retract within grooves 122, as shown in FIG. 5A. Where the spines 118 do not retract, the leaves 102 are still capable of collapsing into a group, as shown in FIG. 5A, when the shape memory alloy of the spines 118 is not activated by the energy source.

Figure 6A:
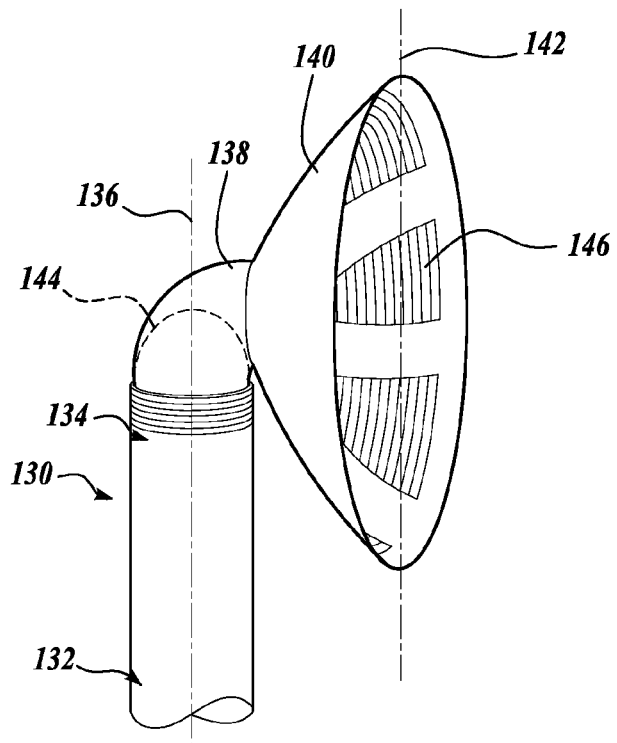
FIGS. 6A and 6B illustrate an implementation of an apparatus with a flexible material coupling a HIFU therapy transducer to a probe.
Figure 6B:
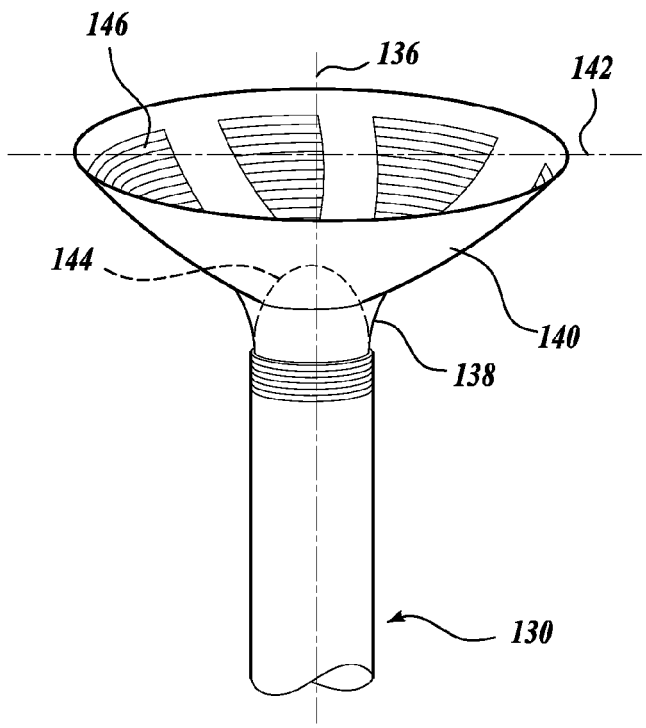

Turning now to FIGS. 6A and 6B, another implementation comprises an elongate probe 130 having a proximal end 132, a distal end 134, and a longitudinal axis 136 extending therebetween. As with other implementations herein, the proximal end 132 of the probe 130 may have a section adapted for positioning the distal end 134 of the probe at a desired location within a patient's body when the probe 130 is inserted into the patient.

The distal end 134 of the probe 130 is fitted with a flexible material 138 that couples a HIFU therapy transducer 140 to the probe 130. The HIFU therapy transducer 140 has an aperture of a size sufficient to direct therapeutic HIFU energy to a treatment site in the patient. For reference purposes, the HIFU therapy transducer 140 has a major axis 142 extending across its face.

In a resting state, as shown in FIG. 6B, the flexible material 138 couples the transducer 140 to the probe 130 in a therapy position wherein the major axis 142 of the transducer is non-parallel to the longitudinal axis 136 of the probe. To facilitate insertion of the probe 130 in a patient's body, e.g., through the vaginal introitus, the flexible material 138 is configured to stretch and allow the transducer 140 to be drawn to the side of the probe 130 to an insertion position as shown in FIG. 6A. In the insertion position, the major axis 142 of the transducer 140 is generally parallel to the longitudinal axis 136 of the probe 130. This allows the largest dimension of the transducer 140 to be in the sagittal axis of the vaginal introitus. The flexible material 138, thus stretched, exhibits a bias to return toward its resting state as shown in FIG. 6B. After the probe 130 has been inserted into the intended cavity of a patient's body, such as the vaginal cavity, the transducer 140 is released from the insertion position and allowed to return to the therapy position shown in FIG. 6B.

If desired, an actuator may be coupled to the HIFU therapy transducer 140 to draw the transducer 140 to the side of the probe 130 while the probe is either being inserted into the patient or withdrawn from the patient. The actuator may also be manipulated to deploy the transducer 140 to the therapy position shown in FIG. 6B. Suitable actuators include, but are not limited to, a cable and/or a latch that can pull, push, and/or hold the transducer in an insertion position as shown in FIG. 6A or in a therapy position as shown in FIG. 6B. In at least one implementation, manipulating the actuator to deploy the transducer 140 may simply involve releasing the transducer and allowing the flexible material 138 to place the transducer in a therapy position. In another implementation, the actuator may actively move the transducer 140 to the desired therapy position.

As with other implementations previously described, the distal end 134 of the probe 130 may include an imaging component 144 adapted for producing an image of a portion of the patient's body when the probe 130 has been inserted in the patient. Preferably, the image produced by the imaging component includes the treatment site receiving the HIFU energy from the transducer 140 to help guide the delivery of the HIFU energy to the treatment site. In one implementation, the imaging component may be configured to use reflected ultrasound energy to produce the image of the portion of the patient's body. In an alternative implementation, the imaging component may be configured to use reflected light to produce the image. In either case, the image produced by the imaging component may further include a portion of the HIFU therapy transducer 140 to assist in positioning the transducer 140 within the patient's body and in monitoring the HIFU therapy occurring at the treatment site.

In a suitable implementation, the flexible material 138 may be comprised of a resilient, non-metal material, such as a medical grade plastic, rubber, or silicon. In an alternative implementation, the flexible material 138 may be comprised of a shape memory alloy having a stretched state or resting state dependent on energy activation of the alloy. The shape memory alloy may be activated to assume a predefined shape based on energy supplied to the alloy which typically heats the alloy and causes the change in shape. Details regarding the structure and use of shape memory alloys have been discussed earlier herein.

Also, as with earlier described implementations, an active element 146 may be disposed on the HIFU therapy transducer 140, wherein the active component is operable to generate the HIFU energy that the transducer 140 directs to the treatment site. Alternatively, the HIFU therapy transducer 140 may be configured with a surface that reflects HIFU energy toward the treatment site. The HIFU energy in this latter implementation may be received from a source that is remote from the transducer 140. Materials, such as a reflective Mylar, capable of reflecting ultrasound energy that is incident thereon, are known in the art.

In yet another implementation of an apparatus constructed according to the present invention, a probe 160, as shown in FIGS. 7A and 7B, may be used to treat pathologies in a patient's body. To facilitate insertion of the probe 160 in the patient, the probe 160 is configured with a HIFU therapy transducer formed of one or more inflatable bladders.

As with prior implementations, the elongate probe 160 has a proximal end 164 and a distal end 166. The proximal end 164 preferably has a section adapted for positioning the distal end 166 of the probe at a desired location when the probe 160 is inserted into a patient's body. The distal end 166 of the probe 160 is fitted with a flexible material having one or more inflatable bladders that, when inflated, provide the HIFU therapy transducer 162. The transducer 162 has an aperture of a size sufficient to direct a focused beam of therapeutic HIFU energy to a treatment site in a patient. The inflatable bladders may be constructed of an expandable material, such as (but not limited to) rubber or silicon.

The one or more inflatable bladders 168 extend radially outward from the distal end 166 of the probe 160. The bladders 168 are not inflated until after the probe is inserted into the intended cavity of the patient's body, such as through the vaginal introitus into the vaginal cavity. After insertion, the bladders 168 are inflated to form the HIFU therapy transducer 162 and to provide lateral support to the HIFU therapy transducer 162 within the patient's body. When inflated, the transducer 162 has an aperture that is larger than the diameter of the probe 160. Appropriate conduits for delivering a pressurized fluid, such as a liquid or gas, to the inflatable bladders 168 are provided within the probe 160 and coupled to the bladders 168. Likewise, conduits are provided to conduct the fluid away from the bladders 168 when the bladders are deflated. If desired, the fluid (liquid or gas) may be circulated to and from the bladders 168 and cooled to help manage the temperature of the transducer 162 and/or tissue adjacent to the transducer 162 when HIFU therapy is being applied.

As further depicted in FIG. 7B, the flexible material forming the HIFU therapy transducer 162 has a front surface 170 adapted to direct HIFU energy to the treatment site in the patient when the probe 160 is inserted and the bladders 168 are inflated.

In the implementation illustrated in FIGS. 7A and 7B, the bladders 168 comprise one or more inflatable channels that extend radially outward from the distal end 166 of the probe 160. The front face 170 of the flexible material extends between the inflatable channels 168.

If desired, the inflatable channels 168 may terminate in an inflatable ring 172 that forms an outer edge 174 of the HIFU therapy transducer 162. The ring 170, when inflated, provides further support to the HIFU therapy transducer 162 and maintains the aperture of the transducer for delivery of HIFU therapy to the patient. When inflated, the diameter of the ring 172, measured as a cross-section of the ring, is larger than the diameter of the probe 160, measured at the distal end 166 of the probe.

In FIG. 7B, the front surface 170 of the flexible material is shown with one or more active elements 176 that are operable to generate HIFU energy that is directed by the transducer 162 to the treatment site in the patient. As noted earlier, HIFU generating elements are known in the art. Conduits for providing energy to the active element 176 are provided within the probe 160. Alternatively, the front surface 170 may be configured with a material that reflects HIFU energy toward the treatment site. As with other implementations described herein, the HIFU energy may be received from a source that is remote from the flexible material.

Additionally, as with other implementations described herein, the distal end 166 of the probe 160 may further include an imaging component 178 adapted for producing an image of a portion of the patient's body that includes the treatment site. Imaging of the patient in this manner may help guide the delivery of HIFU energy to the treatment site. The imaging component 178 may be configured to use reflected ultrasound energy or reflected light to produce the image, as described earlier herein. The image produced by the imaging component 178 may further include a portion of the HIFU therapy transducer 162 to assist in positioning the transducer within the patient's body and in monitoring HIFU therapy being delivered at the treatment site.

FIG. 8 illustrates an implementation of a probe 180 that is likewise fitted with a flexible material having an inflatable bladder that, when inflated, provides a HIFU therapy transducer 182. The transducer 182 may include one or more active elements 184, as shown, or provide a reflective mirror surface that reflects HIFU energy toward the treatment site. In contrast to the implementation with inflatable channels 168 shown in FIGS. 7A and 7B, FIG. 8 depicts an implementation with a single inflatable bladder 186 that, when inflated, is capable of providing HIFU therapy to a patient. To facilitate insertion of the probe 180 in the patient's body, the bladder 186 is not inflated until after the probe is inserted in the intended cavity of the patient's body. The bladder 186, when inflated, forms and provides lateral support to the HIFU therapy transducer 182.

Figure 9A:
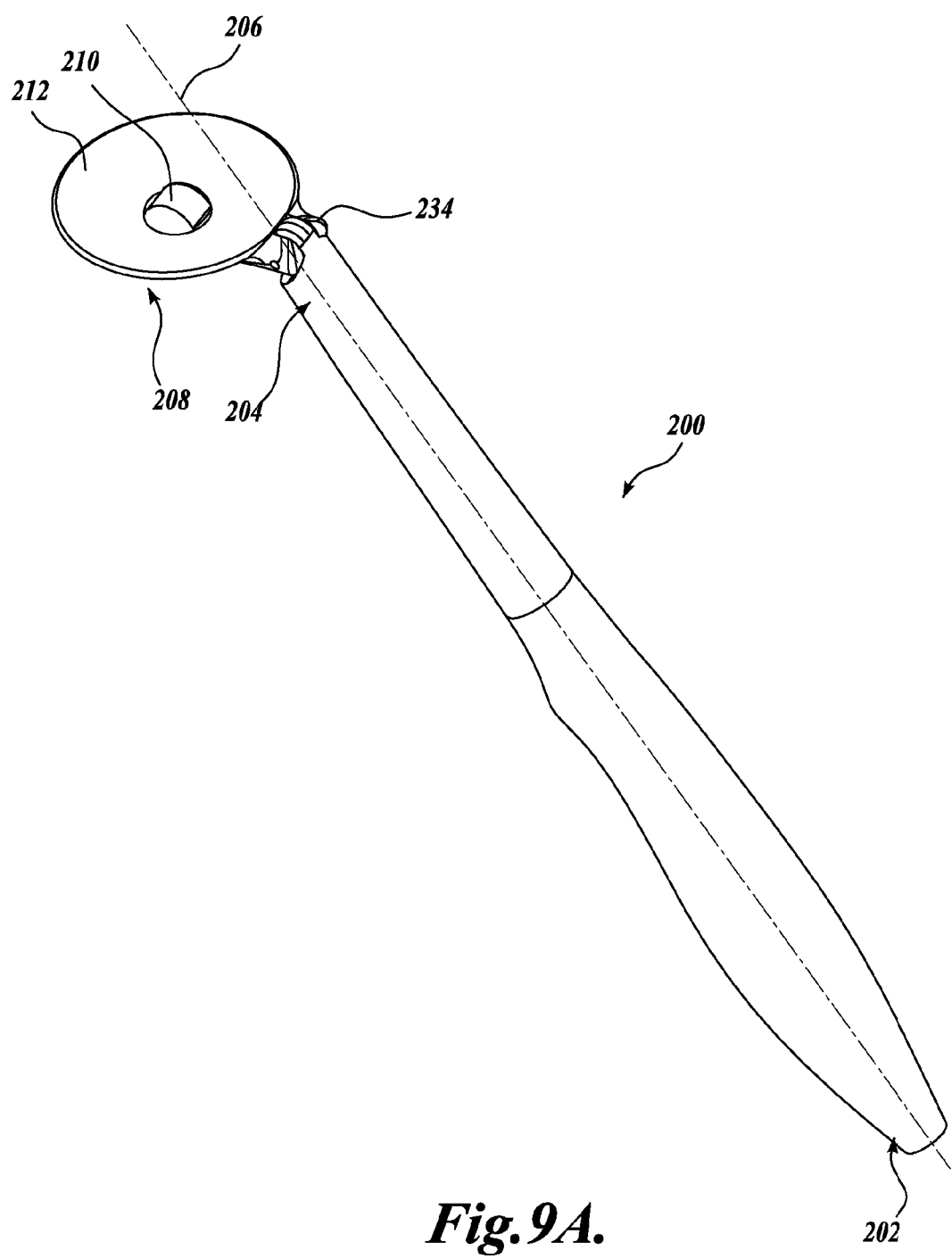
FIGS. 9A and 9B illustrate further aspects of an implementation with an imaging component and HIFU therapy transducer as a unit configured to rotate about a hinge, where the imaging component is disposed within the interior of the HIFU therapy transducer.
Figure 9B:
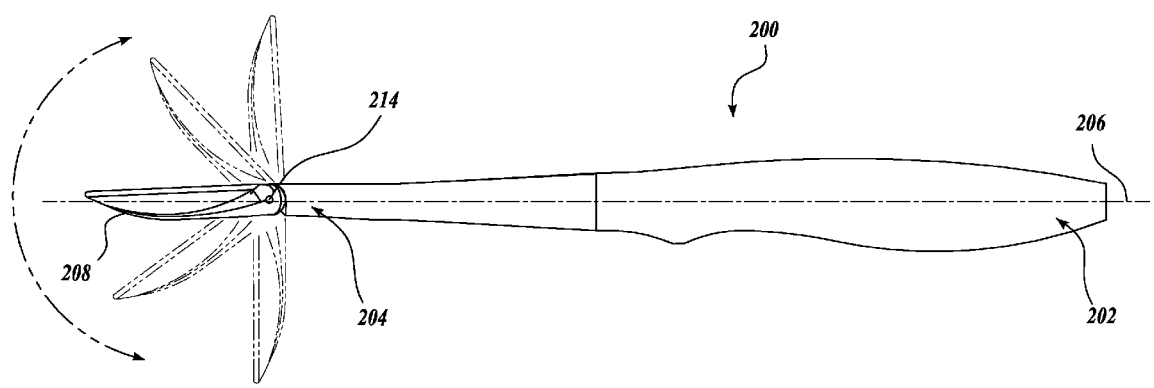

Turning now to FIGS. 9A and 9B, an apparatus for delivering HIFU energy to a treatment site internal to a patient's body is shown in accordance with another implementation of the invention. The apparatus includes an elongate probe 200 having a proximal end 202, a distal end 204, and a longitudinal axis 206 extending therebetween. The proximal end 202 of the probe 200 preferably has a section adapted for positioning the distal end 204 of the probe at a desired location within the patient's body.

Further depicted in FIGS. 9A and 9B is a support structure 208 having an imaging component 210 and a HIFU therapy transducer 212 disposed thereon. A hinge 216 connects the support structure 208 to the distal end 204 of the probe 200.

The imaging component 210 is adapted for producing an image of a portion of the patient's body that includes the treatment site, while the HIFU therapy transducer is adapted for delivering HIFU energy to the treatment site. The HIFU therapy transducer has an aperture of a size sufficient to direct therapeutic HIFU energy to the treatment site and is disposed on the support structure 208 in defined relation to the imaging component 210. In the particular implementation shown, the HIFU therapy transducer 212 is bowl-shaped, and the imaging component 210 is disposed within the interior of the therapy transducer 212.

To facilitate insertion of the probe 200 in the patient's body, e.g., through the vertical axis of the vaginal introitus, the support structure 208 is capable of rotating about the hinge 214 to an insertion position generally parallel to the longitudinal axis 206 of the probe 200, as shown in FIG. 9B. In at least one implementation, the dimension of the therapy transducer 212 in its insertion position and measured perpendicular to the longitudinal axis 206 of the probe is smaller than the dimension of the transducer 212 measured parallel to the longitudinal axis 206. The hinge 214 provides an articulation that enables the imaging and therapy transducers 210, 212 as a unit to be positioned relative to the treatment site in the patient's body. In this implementation, the alignment of the imaging and HIFU therapy is maintained, thus maintaining the focal range of the HIFU therapy field in the same region on the image plane. Advantageously, this region can determined and calibrated at the factory. Thereafter, as a result, software control of HIFU transducer will be simpler.

After insertion of the distal end 204 of the probe 200 in a patient's body, the support structure 208 is capable of rotating about the hinge 214 to a position non-parallel to the longitudinal axis 206 of the probe 200, as may be desired to effectively aim the HIFU energy from the therapy transducer 212 to the treatment site in the body. By rotation, the HIFU therapy transducer 212 can also be placed in a better position for coupling to a bodily structure, such as the uterine cervix of a female patient.

Figure 10A:
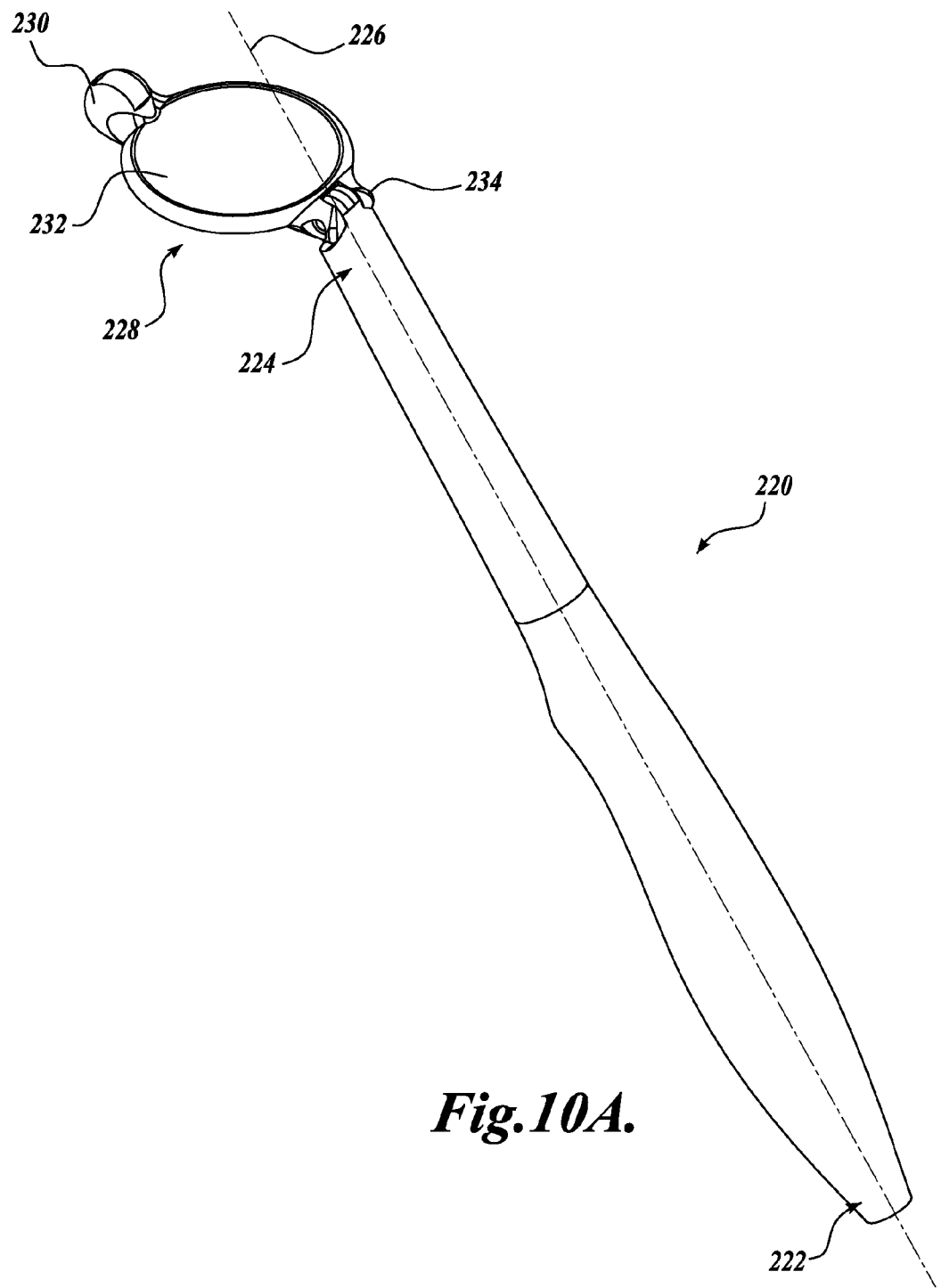
FIGS. 10A and 10B illustrate further aspects of an implementation similar to the implementation shown in FIGS. 9A and 9B, where the imaging component is disposed to the exterior of the HIFU therapy transducer.
Figure 10B:
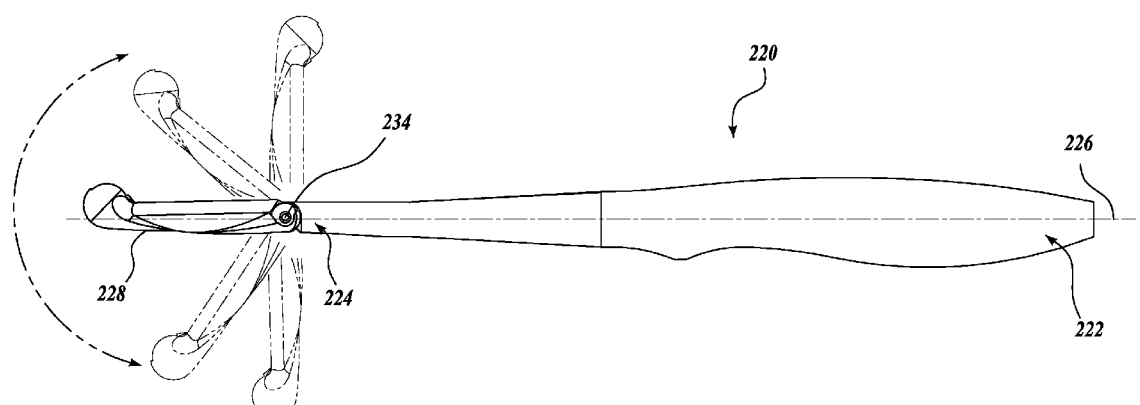

Lastly, FIGS. 10A and 10B depict an elongate probe 220 having features similar to those shown in the probe 200 of FIGS. 9A and 9B. The probe 220 has a proximal end 222, a distal end 224, and a longitudinal axis 226 extending therebetween. A support structure 228 bearing an imaging component 230 and a HIFU therapy transducer 232 is rotatable about a hinge 234 connected to the distal end 224 of the probe 220.

In contrast to the probe 200 shown in FIGS. 9A and 9B, the imaging component 230 shown in FIGS. 10A and 10B is disposed on the support structure 228 to the exterior of the HIFU therapy transducer 232. Having the imaging transducer to the exterior of the therapy transducer in some circumstances may provide a more advantageous angle for imaging the treatment site and the effects of the HIFU therapy being delivered thereto.

In a suitable implementation, the imaging component 230 as well as the imaging component 210 may be configured to use reflected ultrasound energy to produce an image of a portion of the patient's body. In other suitable implementations, the imaging component 230 and/or the imaging component 210 may be configured to use reflected light to produce a visual image. Where reflected ultrasound energy is used to produce the image, an implementation of the invention may use the same transducer, such as the transducers 212 and/or 232, to perform both the imaging and delivery of HIFU therapy. Appropriate synchronization of the imaging and HIFU pulses will be desired. Nevertheless, in such cases, an imaging component 210, 230 separate from the therapy transducer 212, 232 is not necessary. If a portion of the HIFU therapy transducer is shown in the image, the image may further assist in positioning the HIFU therapy transducer within the patient's body and in monitoring the delivery of HIFU therapy at the treatment site.

An overall control system for the above-described probes can be implemented using computer hardware and/or software. A control system may provide tools for clinicians to program a treatment strategy for a specific region of interest in the body. The tools may include setting various focal lengths to treat a two-dimensional or three-dimensional region in the tissue, setting an appropriate power level for excitation of the HIFU transducer to obtain a desired intensity at the focus (either for a single element HIFU or a multi-element HIFU transducer) based on expected attenuation of the tissue between the HIFU transducer and the focus, setting a duration of the HIFU application, setting a threshold for power above which the system should shut down for safety purposes, and setting a duty cycle of the HIFU exposure with respect to ultrasound image acquisition. An interface may also provide tools for the clinician to override the computer plan and design a treatment plan based on their discretion. Advantageously, this interface may provide tools to define in two dimensions or three dimensions the region of body that needs to be treated, and appropriately provide possible approaches to the treatment of that region using the information of the focal length variations (mechanical or electronic). The interface may continually update the clinician of the stage of the treatment and the next steps to be taken, as well as advise whether the plan should proceed or be altered. Finally, the interface may continually interrogate the acoustic path (pre- and post-focal) for bone and gas interfaces that could potentially result in excessive energy deposition, leading to potential undesired tissue damage.

The operation of the HIFU and imaging transducers may be based on an electronic control system that allows proper synchronization of HIFU and imaging pulses. The HIFU driving electronics may be based on radio frequency (RF) amplifiers that are driven by excitation signals obtained from function generators. The amplifier and the function generator could potentially be implemented in one unit. The synchronization of the HIFU application could be done at either the function generator or the RF amplifier stage. For the case of multiple-element HIFU transducers, a multi-channel HIFU system may be used. Each channel of the multi-channel system is preferably capable of being driven with varying phase to allow proper focusing of the HIFU transducer on various spots in the body.

In some applications, HIFU energy is purposefully directed to destroy tissue in multiple target areas to ablate a volume of tissue, such as the endometrial tissue in the uterus. Maximal tissue destruction within the target areas can be achieved with minimal effort, energy, and time required while also minimizing potential collateral damage to the tissue surrounding the target areas. Direct real time visualization of the pelvic organs and of HIFU lesions within the target tissue is useful, particularly when ablating the entire endometrial tissue layer and the superficial myometrial layer of a patient, or in the case of cervical neoplasia, the entire lesion(s) in the patient. Examples of these applications are described as follows.

Endometrial Ablation

One exemplary method employs HIFU energy to target some or all of the endometrial surface, including the full thickness of the endometrium through the basal layer into the superficial layer of the underlying myometrium. This method results in ablation of the endometrium. The HIFU energy may also cause blood vessels in the treated area to be occluded, which further enhances the destruction of the endometrial tissue by ischemia. This may prevent future endometrial tissue regeneration. In patients with adenomyosis, the methods described herein may further result in occlusion of the adenomyosis pockets, especially in view of the vascular occlusion effect, to prevent regeneration of endometrial tissue from those adenomyosis pockets in the myometrium. Desirably, procedures for endometrial ablation may be carried out using an apparatus that provides real-time transvaginal ultrasound image-guided HIFU therapy.

When ablating endometrial tissue, both coverage and depth of penetration of the HIFU energy are addressed to achieve optimal results. As to coverage, the entire endometrial surface is ablated to destroy the endometrium. This can be especially important in cases of patients having a larger than normal size uterine cavity, irregular shaped uterine cavity and/or cavity with irregular contour of the endometrial surface, such as caused by fibroids. As to depth of penetration, the entire thickness of the endometrium, including the basal layer and preferably the superficial layer of underlying myometrium, is destroyed.

Normally, ablation of endometrial tissue at a depth of approximately 6 mm will cover the full thickness of the endometrium, including the basal layer and the superficial layer of the myometrium. The HIFU focus spot size can be adjusted to various sizes, shapes, and orientation to provide a uniform layer of tissue ablation of a thickness in the 6 mm range. Furthermore, by using real-time ultrasound image guidance, the HIFU focus size, shape, and orientation can also be adjusted to thicken or thin down in specific target areas for efficacy and safety considerations. For example, in the cornual area, the myometrium can be thin, so the ablation layer can be adjusted to be thinner as directed by real-time ultrasound imaging. On the other hand, in the area of thickened endometrium, the ablation thickness can be adjusted upward.

Using real time ultrasound imaging to guide the transvaginal HIFU treatment, the endometrial cavity can be visualized simultaneously while the HIFU energy is being applied. One major drawback for most global endometrial ablation techniques in the prior art is the lack of visualization of the endometrial cavity during treatment. It is especially difficult for most global endometrial ablation techniques to treat uterine cavities of larger than normal size or uterine cavities with irregular contours. By using real-time ultrasound imaging, the endometrial surface can be visualized throughout the HIFU treatment and thus the treatment can follow the contour of the entire endometrial cavity to treat the whole surface area, irrespective of the size and shape of the uterine cavity.

To perform endometrial ablation using high intensity focused ultrasound energy, a transvaginal probe is positioned in the vagina of the patient, with the distal end of the probe positioned adjacent to the uterus. As previously described herein, the probe includes a transducer that is deployable in the vagina of the patient outside of the cervix and uterine cavity. In this particular example, the transducer is configured to direct HIFU energy to a treatment site within the uterus of the patient.

When the HIFU transducer is energized, the energy emitted from the transducer produces a thermal heating of the tissue at the focus to initiate necrosis of the tissue. To direct the HIFU energy to the tissue in the uterus to be ablated, the location of the focus may be controlled in accordance with one or more images obtained from an imaging component. The imaging component is positioned relative to the patient to image a portion of the patient's uterus that includes the treatment site. Much like the probe, the imaging component may be positioned within the vagina outside of the cervix and uterine cavity.

Ideally, the location of the focus is controlled in real time while the HIFU transducer is energized. The imaging component provides real time visualization of the effects of the HIFU therapy at the treatment site. Moving the focus through a volume of tissue within the uterus causes the HIFU energy to ablate the volume of tissue. Furthermore, moving the treatment site within the uterus causes the HIFU energy to ablate additional volumes of tissue in the uterus. When the volumes of tissue comprise the endometrial tissue of the patient, a minimally invasive procedure for endometrial ablation is accomplished.

Software and/or hardware controls may be used to move the HIFU focus in such a way that the HIFU focus will systematically cover a target area with a programmed area size and shape and also depth of penetration. The coverage area may vary in size, ranging from a small area, covering a limited area of the uterine cavity or cervix, to the entire surface area of a target, such as the endometrium or a cervical lesion. The input for the programmed area of ablation and the depth of penetration at various points of coverage can be set by the operator, in conjunction with the real time ultrasound image information obtained in terms of surface area, contour, pathologies present, and tissue ablation requirements. Technology for implementing such a method is presently available in use, e.g., for ground contour guidance for flight and for use by laser resurfacing programs, and can be adapted for use in the present invention in accordance with the description provided herein.

The imaging component may be positioned relative to the probe, or alternatively, in a fixed relationship to the probe. In a fixed relationship, an adjustment in the position of the either the imaging component or the probe will cause the position of the other to also be adjusted. Thus a joint positioning of the probe and the imaging component can be achieved. In a relative relationship, the position of the imaging component or the probe may be adjusted without necessarily affecting the position of the other. In some cases, the imaging component may be positioned separately from the probe outside the vaginal cavity. For example, the imaging component may be positioned abdominally on the patient.

In an embodiment where the positioning of the imaging component and probe is relative to the other, one or more sensors may be included with the imaging component or probe that enable the operator to observe the change in relative position when the position of the imaging component or probe is adjusted. For example, signals exchanged between small power RF emitters/receivers on the imaging component and probe can be used to sense the relative position of the two instruments. Alternatively, a separate electronic instrument may be used to sense the relative position of the imaging component and the probe.

Advantageously, it has been found that infusing a liquid media into the endocervical canal and/or uterine cavity may enhance the ultrasound imaging of the endometrium by the imaging component. The liquid media may also enhance the therapeutic effectiveness of the HIFU therapy delivered from the probe to the treatment site. For instance, maintaining an infusion of liquid media in the uterine cavity during imaging and delivery of the HIFU therapy may help clearly outline the contour of the uterine cavity and the surface of the endometrium for ablation of the endometrium. As may be desired for different applications, the liquid media may have a lower viscosity that enhances fluid flow of the medium, or have a higher viscosity as that of a gel.

In some cases, the liquid media may contain physical particles or microbubbles that enhance the imaging and/or therapeutic effect of the ultrasound energy, particularly if the particles or microbubbles are configured to synergistically interact with the HIFU energy at the treatment site. In an embodiment, for example, graphite particles or microbubbles in the liquid media could be sized in accordance with the frequency of the HIFU energy being applied. In this manner, the particles and/or microbubbles can be tuned so as to maximize the absorption of energy at the focus of the HIFU beam, thus allowing a greater transfer of energy for thermal heating at the focus.

By enabling the liquid medium to enhance the transfer of energy at the focus, the amount of energy needed in the HIFU beam may be reduced. Such an embodiment may also require a lower accuracy in targeting of the HIFU beam, thus potentially reducing the required skill level of the operator of the probe. In addition, by absorbing a greater amount of the HIFU energy at the focus, the liquid medium can help minimize post-focal scattering of the energy, thus reducing the risk of collateral damage to adjacent tissue. Furthermore, in locations in the uterine cavity and/or endocervical canal where different sides of tissue come into proximity, localized heating of the liquid medium in the cavity or canal may cause simultaneous ablation of both sides of the cavity or canal, resulting in a faster ablation procedure.

Physical particles, such as a graphite material, may be added to the liquid medium before the liquid medium is infused into the uterine cavity or endocervical canal. Likewise, microbubbles may be added or generated in the liquid medium before it is infused into the uterine cavity or endocervical canal. As to the latter, in one example, an agitated saline may be used to provide the microbubbles. Depending on the particular procedure used, microbubbles of different sizes may be generated in the liquid medium. Different size microbubbles can have different effects depending on the HIFU energy being applied. Yet other embodiments may infuse a liquid medium comprised of mixture of liquids, such as a saline and mineral oil, to increase localized selective absorption of the HIFU energy in the uterine cavity or endocervical canal, dependent on the HIFU energy being applied and the thermal heating effects desired.

In some cases, it may not be necessary or appropriate to infuse a liquid medium (with or without additional particles or microbubbles) into the uterine cavity and/or endocervical canal. In some cases, a concentration of HIFU energy may naturally occur at the interface between the sides of the endometrium without an infusion of liquid between the sides of the endometrium. This results, in part, due to the proximity of the tissue being ablated. Additionally, a slight change in tissue densities or attenuation at the endometrial interface may tend to selectively reflect or absorb the HIFU energy. Thus, some embodiments of the invention may produce an effective uterine tissue ablation without fluid media being added to the uterus.

The liquid media may also incorporate drugs or medications, including but not limited to, local anesthesia or analgesics, to be infused into the uterine cavity and/or the endocervical canal or applied to the cervix. These drugs in the liquid media can provide anesthetic and analgesic effect to the patient before, during, and after the HIFU treatment procedure to make it more tolerable to have the procedure performed, with or without general or regional anesthesia. In circumstances where the drug in the liquid media is an anesthetic or analgesic, localized pain that the patient may feel as a result of application of HIFU therapy may be mediated.

It has further been found that positioning a seal at the cervical canal, either at the anterior or posterior end, can help maintain the liquid media in the uterus. A seal is particularly advantageous when the liquid media is maintained at a positive pressure in the uterus. By controlling the pressure of the liquid media, the contour and/or shape of the tissue in the uterine cavity can be modified, which can aid in the HIFU treatment.

For example, the thickness of the endometrial tissue in the uterus may be altered to optimize HIFU ablation of the endometrium. Increasing the pressure of the liquid media may compress the endometrial tissue in the uterine cavity. Compressed tissue generally requires less depth of penetration of HIFU energy and possibly less time for ablation of the tissue. Modifying the shape of the tissue in the uterine cavity by adjusting the pressure of the liquid media may also provide a means to adjust the location of focus of the HIFU therapy without moving the HIFU transducer or adjusting the parameters of the HIFU pulse.

In some circumstances, maintaining a liquid medium in the endocervical canal and/or the uterine cavity at a positive pressure may cause a material in the liquid medium to the penetrate into the tissue of the treatment site. In other words, increasing the pressure of the infused liquid medium may also increase the penetration of particles, microbubbles, or drugs into the endometrium/myometrium to enhance HIFU ablation.

Figure 11:
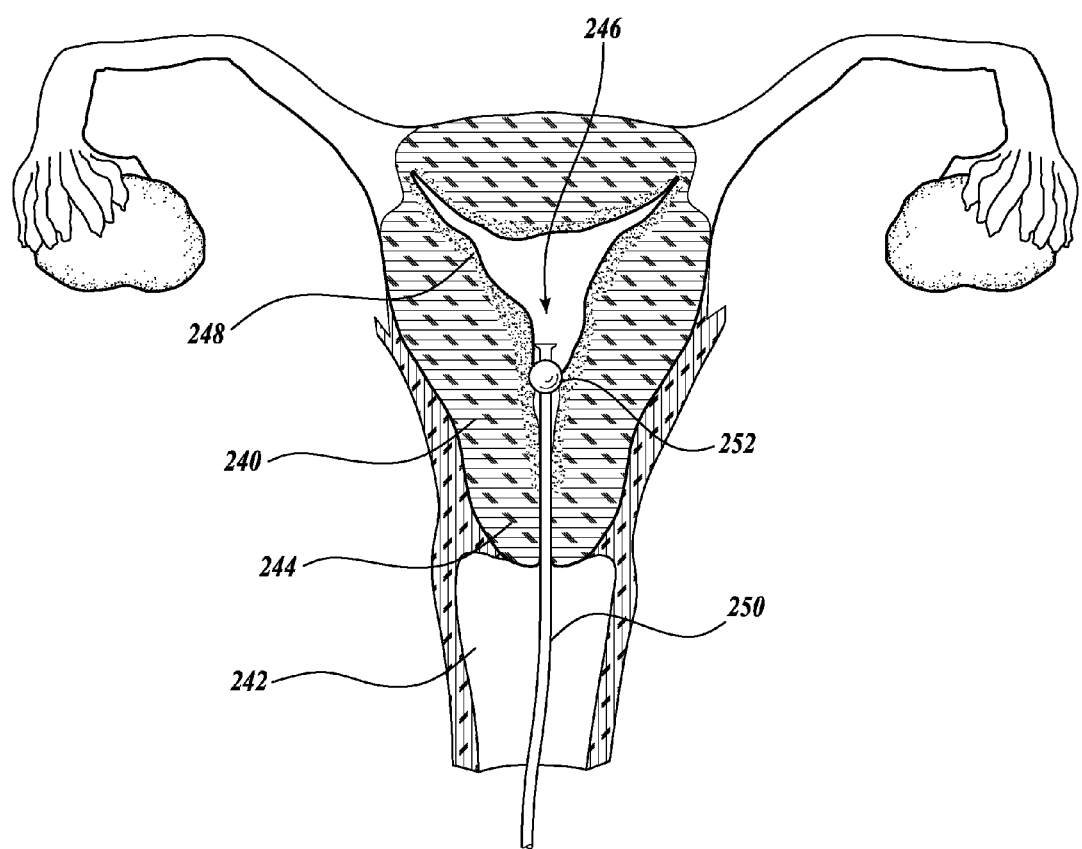
FIG. 11 illustrates a transport line with a seal for infusing a liquid medium into the uterine cavity, which may be used to enhance the imaging and HIFU therapeutic effect for endometrial/cervical ablation procedures.

FIG. 11 illustrates a uterus 240 having a uterine cavity 246. Below the uterus 240 is a vaginal cavity 242. The uterine cavity 246 is connected to the vaginal cavity 242 via the cervix 244. The uterine cavity 246 is lined with endometrial tissue 248.

FIG. 11 further depicts an embodiment of a transport line 250 that may be used to infuse a liquid medium into the uterine cavity 246. As noted above, the liquid medium may be used to enhance the imaging and HIFU therapeutic effect for endometrial and/or cervical ablation procedures. The transport line 250 may comprise a thin flexible or rigid catheter of appropriate caliber, and preferably is made of a bio-compatible material. The transport line 250 is adapted for insertion through the vagina 242 to carry the liquid medium at least to the cervix 244. As will be understood herein, the transport line 250 is capable of infusing the liquid medium into the endocervical canal of the cervix 244 and/or the uterine cavity 246 of the patient and maintaining the liquid medium in the endocervical canal and/or uterine cavity during imaging and delivery of HIFU energy to the treatment site.

In FIG. 11, the transport line 250 has been inserted through the cervix 244 into the lower portion of the uterine cavity 246. Liquid media in the transport line 250 is thereafter allowed to fill the uterine cavity. Alternatively, the opening of the transport line 250 can initially be positioned near the top of the uterine cavity 246, where the liquid media is injected to fill the cavity 246 from the top of down, thus pushing out and replacing any gas or fluid that is present in the uterine cavity. If the opening of the transport line 250 is positioned at the entry of the cervix 244, the liquid media can be infused into the uterus through the endocervical canal.

Various configurations of the transport line 250 may be used to infuse liquid media into the uterus. For example, the transport line 250 may have a single lumen for both injection and extraction of the liquid media, or alternatively, there can be a second lumen, within the transport line or circumferentially around the transport line.

A seal 252 may be provided at the anterior and/or posterior end of the endocervical canal to assist with maintaining the liquid medium in the uterus, particularly when a positive pressure of the liquid medium in the uterus is desired. Various configurations of seals may be used. For example, one or more balloons may be incorporated in the surface of the transport line 250 at one or more strategic positions along the length of the transport line. Inflation of the balloon or balloons on the transport line 250 can stabilize or fix the transport line in the uterine cavity and/or the endocervical canal. Additionally, the balloon or balloons can seal the orifices of the uterine cavity or endocervical canal for fluid flow or pressure management within those spaces. In FIG. 11, the seal 252 is shown sealing the endocervical canal on the posterior side toward the uterine cavity 246. Sealing structures that may be adapted for use with the present invention may be drawn, for example, from existing technologies, such as those disclosed by Marsella et al., U.S. Patent Application Publication No. 2007/0066990, and Hibler, U.S. Pat. No. 7,105,007, both of which are incorporated herein by reference.

Another iteration of this embodiment or other embodiments involves incorporating the transport line 250 into the transvaginal probe, with the ultrasound transducer(s) at the distal end of the probe, so as to allow the transport line to manipulate and move the endocervical canal or the uterus to an optimal position for ultrasound imaging and/or HIFU therapy by the transducer(s). This embodiment is particularly useful if the transport line is comprised of a more rigid material. In addition, when the transport line 250 is integrated with the probe 1 shown in FIG. 1, for example, the coupling 5 shown in FIG. 1 may be used to carry the liquid media or it may incorporate a separate lumen or channel to carry the liquid media to the transport line 250. The liquid media in this instance is preferably (though not necessarily) separate from the cooling fluid used for coupling the HIFU transducer 2 to the uterine tissue.

Cervical Neoplasia

Using transvaginal real time ultrasound imaging, the cervix including the endocervical canal can be visualized while simultaneously applying HIFU energy to localized lesions. HIFU energy is shown effective to ablate the diseased tissue with precision in terms of both surface coverage and depth of penetration. The precise depth of penetration of the tissue ablation into the cervix ensures that all the neoplastic lesions, including those involving the endocervical glands, are destroyed while limiting collateral damage to the normal cervical tissue.

Figure 12:
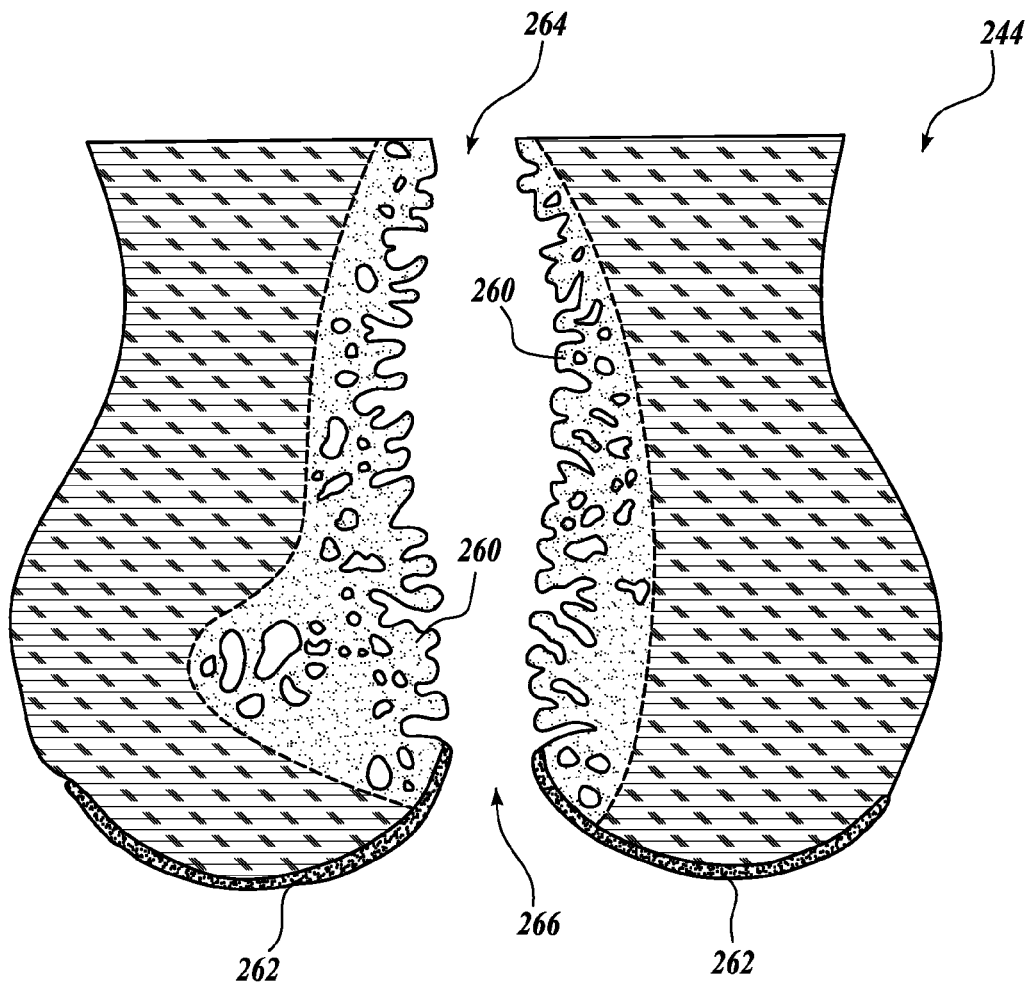
FIG. 12 illustrates a cervix having a defined volume of tissue with cervical lesions (CIN) to be ablated using transvaginal image-guided HIFU therapy as described herein.

FIG. 12 illustrates a cervix 244 having a defined volume of tissue 260, 262 to be ablated using transvaginal image-guided HIFU therapy as described above. Additionally, if desired, a liquid medium can be applied to the cervix to aid the coupling between the cervix and the ultrasound transducers. The liquid medium can be applied to the cervix and/or infused into the endocervical canal 266 to the internal os 264 to enhance the ultrasound imaging and improve the HIFU therapy being applied, particularly to lesions in the endocervical tissue 260 and/or ectocervical tissue 262. As with the embodiments discussed above for endometrial ablation, the liquid medium applied to or into the cervix 244 may include physical particles, microbubbles and/or drugs to enhance the ultrasound imaging and/or the therapeutic effect of the HIFU energy on the cervical tissue. If desired, the liquid medium may have a higher viscosity as that of a gel.

Thus, in view of the foregoing, it should be readily understood that high intensity focused ultrasound (HIFU) energy may be used for ablation of tissue at or within the cervix of a female patient. A probe with a HIFU transducer may be deployed in the vagina of the patient outside of the cervix. Energizing the HIFU transducer allows the probe to produce a thermal heating of tissue at a focus of the HIFU energy to initiate necrosis of the tissue at the treatment site. Advantageously, real-time imaging of the cervix may produce an image that includes the treatment site to help control the location of the focus and direct the HIFU energy to the cervical tissue to be ablated.

Depending on the treatment to be provided, the focus of the HIFU energy may be controlled to ablate the tissue 260 in the endocervical canal of the patient. The focus of the HIFU energy may also be directed to ablate the ectocervical tissue 262 of the patient. For example, the focus of the HIFU energy may be controlled to ablate neoplastic lesions or human papilloma virus-related lesions in the cervix.

To help maintain the liquid medium in the endocervical canal, a seal may be positioned at the entry of the endocervical canal 266 or at the internal os 264. Examples of seal configurations discussed earlier with respect to FIG. 11 may be adapted for this purpose. If desired, a positive pressure of the liquid medium may be maintained to increase penetration of a material in the liquid medium into the tissue of the treatment site. If a seal is positioned at the internal os 264, as with the seal 252 shown in FIG. 11, the transport line 250 may be capped and instead the liquid media in the transport line may infuse into the endocervical canal through one or more orifices defined along the length of the transport line within the endocervical canal.

For purposes of example only, various implementations have been described above for treating pathologies of the female reproductive system where necrosis of a region of tissue has a therapeutic effect. By way of example, and not by limitation, these implementations can be used to treat uterine fibroids, adenomyoma of the uterus, adenomyosis of the uterus, endometrial polyps, endometrial ablation to achieve reduction or elimination of menstrual flow, endometrial hyperplasia, cornual pregnancy, benign ovarian cysts, pelvic endometriosis, ectopic pregnancy, and malignant lesions of the pelvic organs, whether primary or metastatic. Another alternative embodiment includes a transabdominal HIFU transducer applicator to work in conjunction with the transvaginal image-guided HIFU probe to obtain an optimal focal length of the HIFU therapy to treat the endometrial lining of the various parts of the uterus and also other intended pelvic pathologies.

Although embodiments of the invention have been described in connection with certain depicted implementations, those of ordinary skill will recognize that one or more features of a particular implementation described herein may be used in another implementation for similar advantage. Accordingly, it is not intended that the scope of the invention in any way be limited by the precise forms described above, but instead be determined by reference to the claims that follow and equivalents thereto.

The embodiments of the invention in which an exclusive property or privilege is claimed are defined as follows:

1. A system for treating endometrial tissue in a female patient using high intensity focused ultrasound (HIFU) energy, comprising:
    a HIFU transducer that is configured to emit HIFU energy toward targeted endometrial tissue at a treatment site within the cervix and/or uterus of the patient;
    an imaging component configured to image a portion of the patient's cervix and/or uterus that includes the treatment site to help guide the delivery of the HIFU energy;
    a liquid medium having particles or microbubbles therein that are configured to interact with the HIFU energy at the treatment site to enhance the therapeutic effects of the HIFU energy; and
    a transport line adapted for insertion through the vagina, which is capable of infusing the liquid medium in the endocervical canal and/or uterine cavity during imaging and delivery of the HIFU energy to the treatment site;
    wherein the HIFU transducer is configured to ablate the targeted tissue at or near its focus, the location of which can be controlled in response to images obtained by the imaging component.

2. The system of claim 1, further comprising a sealing structure on the transport line at the anterior and/or posterior end of the endocervical canal to assist with maintaining the liquid medium in the uterine cavity and/or endocervical canal.

3. The system of claim 1, wherein the HIFU transducer and the imaging component are integrated into a probe that is deployable in the vagina of the patient and the transport line is integrated with the probe for insertion through the vagina of the patient.

4. The system of claim 1, wherein the HIFU transducer is a transabdominal HIFU transducer.

5. The system of claim 1, wherein the liquid medium increases localized absorption of the HIFU energy.

6. The system of claim 1, wherein the liquid medium includes a therapeutic drug or anesthetic agent.

7. The system of claim 1, wherein the particles or microbubbles have a size that is tuned to a frequency of the HIFU energy applied.

8. The system of claim 1, wherein the particles are graphite particles.

9. The system of claim 1, wherein the liquid medium is a gel.

10. The system of claim 1, wherein a positive pressure of the liquid medium in the endocervical canal and/or uterine cavity increases penetration of a material in the liquid medium into the endometrial tissue of the patient.

11. A method of using a system for delivering high intensity focused ultrasound (HIFU) energy for ablation of targeted endometrial tissue in a female patient, wherein the system includes a HIFU transducer for emitting HIFU energy, an imager for producing images of the tissue to be ablated, and a transport line for delivering liquid to an endocervical canal and/or uterine cavity, the method comprising:

positioning the HIFU transducer to apply HIFU energy toward a treatment site within the cervix and/or uterus of the patient;

infusing a liquid medium into the endocervical canal and/or uterine cavity of the patient with the transport line, wherein the liquid medium has particles or microbubbles therein that are configured to interact with the HIFU energy at the treatment site to enhance the therapeutic effects of the HIFU energy;

energizing the HIFU transducer to ablate a volume of endometrial tissue; and obtaining an image of at least a portion of the cervix and/or uterus that includes the volume of endometrial tissue being ablated to aid in controlling the delivery of the HIFU energy.

12. The method of claim 11, wherein the particles or microbubbles within the liquid medium are configured to interact with or increase localized absorption of the HIFU energy at the treatment site.

13. The method of claim 11, wherein the transport line includes a seal, the method further comprising positioning the seal to help maintain the liquid medium in the uterine cavity and/or endocervical canal.

14. The method of claim 11, further comprising increasing a pressure of the liquid medium in the uterine cavity and/or endocervical canal.

15. The system of claim 5, wherein the liquid medium is mineral oil or other liquid that inherently affects the localized absorption of HIFU energy in surrounding tissue.

* * * * *